United States Patent
Nadeau et al.

(10) Patent No.: US 9,404,160 B2
(45) Date of Patent: Aug. 2, 2016

(54) METHODS FOR THE DETECTION OF MICROORGANISMS

(75) Inventors: James G. Nadeau, Ellicott City, MD (US); Bernard J. H. Verwer, Phoenix, MD (US)

(73) Assignee: Becton, Dickinson and Company, Franklin Lakes, NE (US)

( * ) Notice: Subject to any disclaimer, the term of this patent is extended or adjusted under 35 U.S.C. 154(b) by 432 days.

(21) Appl. No.: 13/518,211

(22) PCT Filed: Dec. 21, 2010

(86) PCT No.: PCT/US2010/061559
§ 371 (c)(1),
(2), (4) Date: Sep. 13, 2012

(87) PCT Pub. No.: WO2011/087789
PCT Pub. Date: Jul. 21, 2011

(65) Prior Publication Data
US 2012/0329050 A1 Dec. 27, 2012

Related U.S. Application Data

(60) Provisional application No. 61/289,088, filed on Dec. 22, 2009.

(51) Int. Cl.
*C12Q 1/68* (2006.01)

(52) U.S. Cl.
CPC ............ *C12Q 1/689* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,563,419 A | 1/1986 | Ranki et al. |
| 4,851,330 A | 7/1989 | Kohne |
| 5,288,611 A | 2/1994 | Kohne |
| 5,439,797 A | 8/1995 | Tsien et al. |
| 5,518,884 A | 5/1996 | Spears et al. |
| 5,527,675 A | 6/1996 | Coull et al. |
| 5,539,082 A | 7/1996 | Nielsen et al. |
| 5,567,587 A | 10/1996 | Kohne |
| 5,601,984 A | 2/1997 | Kohne |
| 5,612,183 A | 3/1997 | Kohne |
| 5,623,049 A | 4/1997 | Lobberding et al. |
| 5,714,331 A | 2/1998 | Buchardt et al. |
| 5,719,262 A | 2/1998 | Buchardt et al. |
| 5,736,336 A | 4/1998 | Buchardt et al. |
| 5,766,855 A | 6/1998 | Buchardt et al. |
| 5,773,571 A | 6/1998 | Nielsen et al. |
| 5,786,461 A | 7/1998 | Buchardt et al. |
| 5,837,459 A | 11/1998 | Berg et al. |
| 5,843,658 A | 12/1998 | Uchiyama et al. |
| 5,891,625 A | 4/1999 | Buchardt et al. |
| 5,972,610 A | 10/1999 | Buchardt et al. |
| 5,986,053 A | 11/1999 | Ecker et al. |
| 6,083,482 A | 7/2000 | Wang |
| 6,107,470 A | 8/2000 | Nielsen et al. |
| 6,169,169 B1 | 1/2001 | Hyldig-Nielsen et al. |
| 6,174,670 B1 | 1/2001 | Wittwer et al. |
| 6,228,982 B1 | 5/2001 | Norden et al. |
| 6,268,490 B1 | 7/2001 | Imanishi et al. |
| 6,280,946 B2 | 8/2001 | Hyldig-Nielsen et al. |
| 6,280,981 B1 | 8/2001 | Dykens et al. |
| 6,291,201 B1 | 9/2001 | Garman |
| 6,297,018 B1 | 10/2001 | French et al. |
| 6,323,039 B1 | 11/2001 | Dykens et al. |
| 6,342,379 B1 | 1/2002 | Tsien et al. |
| 6,348,322 B1 | 2/2002 | Strittmatter |
| 6,357,163 B1 | 3/2002 | Buchardt et al. |
| 6,395,474 B1 | 5/2002 | Buchardt et al. |
| 6,441,130 B1 | 8/2002 | Egholm et al. |
| 6,451,543 B1 | 9/2002 | Kochendoerfer et al. |
| 6,469,151 B1 | 10/2002 | Egholm et al. |
| 6,472,156 B1 | 10/2002 | Wittwer et al. |
| 6,528,267 B1 | 3/2003 | Coull et al. |
| 6,607,889 B1 | 8/2003 | Coull et al. |
| 6,639,059 B1 | 10/2003 | Kochkine et al. |
| 6,664,045 B1 | 12/2003 | Hyldig-Nielsen et al. |
| 6,670,461 B1 | 12/2003 | Nielsen et al. |
| 6,753,421 B2 | 6/2004 | Stender et al. |
| 7,060,432 B1 | 6/2006 | Hyldig-Nielsen et al. |
| 7,115,364 B1 | 10/2006 | Chee et al. |
| 7,214,783 B2 | 5/2007 | Jeon et al. |
| 7,223,833 B1 | 5/2007 | Nielsen et al. |
| 7,388,092 B2 | 6/2008 | Lee et al. |
| 7,414,118 B1 | 8/2008 | Mullah et al. |

(Continued)

FOREIGN PATENT DOCUMENTS

| | | | |
|---|---|---|---|
| JP | 2003234455 A | | 8/2003 |
| WO | WO-00/65093 | * | 11/2000 |

OTHER PUBLICATIONS

International Search Report PCT/US2010/061559, dated Nov. 28, 2011.
Hwang B. H. et al., "Quanitative Oligonucleotide Microarray data analysis with an artificial standard probe strategy" Biosens, Bioelectron., Jun. 15, 2008, vol. 23, No. 11, pp. 1738-1744 (Epub Feb. 7, 2008).
Amann et al. J. Bacteriol. vol. 172, No. 2, pp. 762-770 (1990).
Amann et al., Appl.Environ.Microbiol. vol. 56, No. 6, pp. (1990), p. 1919 only.
Ausubel et al., Current Protocols in Molecular Biology, vol. 2, Current Protocols Publishing, New York (1994), Table of Contents and p. 11.18.9 only.
Brumbaugh et al., Proc. Natl. Acad. Sci. (USA), vol. 85, pp. 5610-5614 (1988).

(Continued)

*Primary Examiner* — James Martinell
(74) *Attorney, Agent, or Firm* — Lerner, David, Littenberg, Krumholz & Mentlik, LLP

(57) ABSTRACT

Presented herein are methods for the detection of the presence or absence of one or more microorganisms in a sample. The method deploys a plurality of probe sets to detect a plurality of microorganisms. The probes in the probe set are detectably labeled. At least one probe set has probes labeled with a combination of detectable labels. The number of detectable labels used in the plurality of probe sets numbers less than the number of microorganisms being detected by the probe set.

18 Claims, 1 Drawing Sheet

(56) References Cited

U.S. PATENT DOCUMENTS

| | | | |
|---|---|---|---|
| 2003/0027157 A1* | 2/2003 | Fu et al. | 435/6 |
| 2005/0214753 A1 | 9/2005 | Shultz et al. | |
| 2006/0127924 A1 | 6/2006 | Hellyer et al. | |
| 2007/0048968 A1 | 3/2007 | Couillard et al. | |
| 2010/0227452 A1 | 9/2010 | Akiyama et al. | |

OTHER PUBLICATIONS

Car, Can, M. et al., J. Clin. Microbiol. vol. 43, pp. 3023-3026 (2005).
Coligan et al., Current Protocols in Immunology, pp. 8.10.12-8.10.21, eds. John Wiley & Sons, Inc., pub., (1997).
Cox, C., et al, Arthritis Res. Ther., vol. 5, pp. R1-R8 (2002).
DeLong et al., Science vol. 243, pp. 1360-1363 (1989).
Dunn et al., Cell, vol. 12, pp. 23-36 (1977).
Egholm et al., Nature, 365:566-568, (1993).
Greisen, K., J. Clin. Microbiol., vol. 32, No. 2, pp. 335-351. (1994).
Jordan, J., J. Mol. Diag., vol. 7, pp. 575-581, (2005).
Kempf et al., J. Clin. Microbiol., 38:830-838, (2000).
Koshkin et al., J. Am. Chem. Soc., 120:13252-13253 (1998).
Kunishima, S. et al., Transfusion, vol. 40, p. 1420. (2000).
Lakowicz, "Principles of Fluorescence Spectroscopy", Second Edition, pp. 237-265, publisher: Kluwer Academic/Plenum Publisher, (1999).
Lenaerts et al., Appl. Environ. Microbiol., vol. 73, vol. 6, pp. 2020-2023, (2007).
Maaroufi et al., J. Clin. Microbiol., vol. 41, No. 7, pp. 3293-3298, (2003).
McCabe et al., Molecular Genetics and Metabolism, vol. 66, pp. 205-211, (1999).
Perry-O'Keefe et al., J. Microbiol. Methods, vol. 47, pp. 281-292, (2001).
Rothman et al., J. Infect. Dis., vol. 186, pp. 1677-1681, (2002).
Sambrook et al., Molecular Cloning—A Laboratory Manual (2nd Ed.), vols. 1-3, Cold Spring Harbor Laboratory, Cold Spring Harbor, New York (1989), pp xi-xxxviii and 18.88.
Schmidt et al., Meth. Enzymol., vol. 235, pp. 205-222, (1994).
Shalon et al., Genome Res., 6:639-645, 1996.
Stender et al., J. Microbiol. Meth. vol. 48, pp. 1-17, (2002).
Tárnok et al., Cytometry, 50:133-143, 2002.
Wallner et al., Cytometry vol. 14, pp. 136-143, (1993).
White et al., J. Med. Microbiol., vol. 52, pp. 229-238, (2003).
Xi et al., Appl. Environ. Microbiol. vol. 69, pp. 5673-5678 (2003).

* cited by examiner

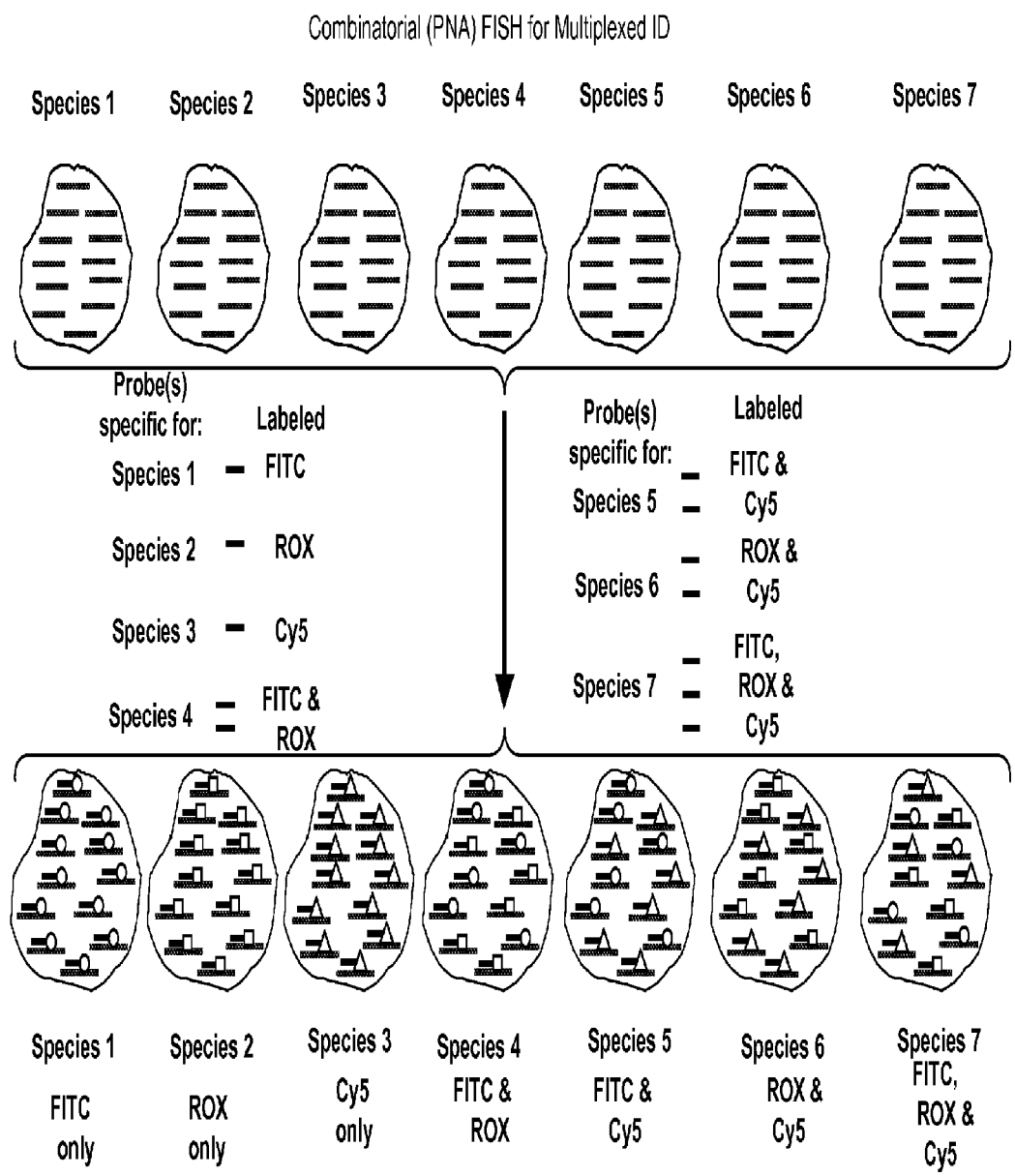

METHODS FOR THE DETECTION OF MICROORGANISMS

CROSS-REFERENCE TO RELATED APPLICATION

The present application is a national phase entry under 35 U.S.C. §371 of International Application No. PCT/US2010/061559, filed Dec. 21, 2010, published in English, which claims the benefit of U.S. Provisional Patent Application No. 61/289,088 filed Dec. 22, 2009, all of which are incorporated herein by reference.

INTRODUCTION

Presented herein are methods for the detection of the presence of one or more microorganisms in a sample.

BACKGROUND

Traditionally, the identity of a microorganism in a given sample has been established by isolating the organism, culturing the organism in a suitable culture medium, and identifying the cultured organism based on biochemical, immunological, and/or other properties.

Because such broad-based culture methods can be laborious and are often slow to yield results, newer molecular biological and immunological methods have emerged that focus on, among other things, the detection of genome nucleic acids, detection of proteins specific to certain microorganisms, and the detection of antibodies directed against certain microorganisms, as means to identify microorganisms in samples tested.

However, despite such progress, there remains a need in the art for rapid, sensitive, and accurate methods for determining the presence of microorganisms in a sample.

SUMMARY

In one aspect, presented herein are methods for the rapid detection of the presence of one or more microorganisms in a sample using probes labeled with combinations of detectable labels. In some embodiments, the methods presented herein utilize probes labeled with combinations of detectable labels, so as to allow for the detection of multiple microorganisms in a sample using a minimum number of detectably-labeled probes, i.e., the total number of detectable labels used in the method is less than the total number of different microorganisms that can be detected in the sample by the method. Such methods take advantage of the fact that probes can be labeled using unique combinations of the same detectable labels, so that each unique combination of detectable labels can be used to detect a different microorganism. Thus, in certain embodiments, the methods presented herein provide for the rapid and straightforward detection of a wide-range of microorganisms using a single multiplex assay. Detection of the presence of one or more microorganisms in a sample can provide information for the selection of the appropriate therapeutic regimen for a patient with a microorganism infection. Methods presented herein may be used to label microorganisms by employing Fluorescence In Situ Hybridization (FISH) techniques which are well known to those skilled in the art and have been described elsewhere (see, e.g., DeLong et al., *Science* Vol. 243, pp. 1360-1363 (1989); Amann et al. *J. Bacteriol.* Vol. 172, pp. 762-770 (1990); Amann et al., *Appl. Environ. Microbiol.* Vol. 56, pp. 1919-1925 (1990); Wallner et al., *Cytometry* Vol. 14, pp. 136-143 (1993); Perry-O'Keefe et al., *J. Microbiol. Methods* Vol. 47, pp. 281-292 (2001); Stender et al., *J. Microbiol. Meth.* Vol. 48, pp. 1-17; Xi et al., *Appl. Environ. Microbiol.* Vol. 69, pp. 5673-5678 (2003); and Lenaerts et al., *Appl. Environ. Microbiol.* Vol. 73, pp 2020-2023 (2007)).

In one embodiment, presented herein is a method for detecting the presence of microorganisms in a sample, comprising:
 (a) contacting the sample with a plurality of detectably-labeled, microorganism-specific probes, wherein said plurality comprises a first probe set comprising a first probe that is specific to a first microorganism, and wherein each first probe in the first probe set comprises a first detectable label and a second detectable label; under conditions that allow hybridization of the probes to a nucleic acid sequence of the first microorganism; and
 (b) assaying for the presence of the hybridized first probes, wherein the presence of the hybridized first probes indicates the presence in the sample of the first microorganism.

In another embodiment, presented herein is a method for detecting the presence of microorganisms in a sample, comprising:
 (a) contacting the sample with a permeabilizing agent and a plurality of detectably-labeled, microorganism-specific probes, wherein said plurality comprises a first probe set comprising a first probe that is specific to a first microorganism, and wherein each first probe in the first probe set comprises a first detectable label and a second detectable label; under conditions that allow hybridization of the probes to a nucleic acid sequence of the first microorganism; and
 (b) assaying for the presence of the hybridized first probes, wherein the presence of the hybridized first probes indicates the presence in the sample of the first microorganism.

In another embodiment, presented herein is a method for detecting the presence of microorganisms in a sample, comprising:
 (a) contacting the sample with a plurality of detectably-labeled, microorganism-specific probes, wherein said plurality comprises a first probe set comprising a first probe that is specific to a first microorganism, and wherein (i) each first probe in the first probe set comprises a first detectable label and a second detectable label and (ii) the first and second detectable labels are at a fixed ratio; under conditions that allow hybridization of the probes to a nucleic acid sequence of the first microorganism; and (b) assaying for the presence of the hybridized first probes, wherein the presence of the hybridized first probes indicates the presence in the sample of the first microorganism.

In another embodiment, presented herein is a method for detecting the presence of microorganisms in a sample, comprising:
 (a) contacting the sample with a permeabilizing agent and a plurality of detectably-labeled, microorganism-specific probes, wherein said plurality comprises a first probe set comprising a first probe that is specific to a first microorganism, and wherein (i) each first probe in the first probe set comprises a first detectable label and a second detectable label and (ii) the first and second detectable labels are at a fixed ratio; under conditions that allow hybridization of the probes to a nucleic acid sequence of the first microorganism; and (b) assaying for the presence of the hybridized first probes, wherein the presence of the hybridized first probes indicates the presence in the sample of the first microorganism.

In another embodiment, presented herein is a method for detecting the presence of microorganisms in a sample, comprising:
- (a) contacting the sample with a plurality of detectably-labeled, microorganism-specific probe sets, wherein said plurality comprises a first probe set specific to a first microorganism comprising a first and second probe, and wherein (i) the first and second probes hybridize to the same nucleic acid sequence, and (ii) the first probe comprises a first detectable label and the second probe comprises a second detectable label; under conditions that allow hybridization of the probes to the nucleic acid sequence of the microorganism; and
- (b) assaying for the presence of the hybridized first probe set, wherein the presence of the hybridized first probe set indicates the presence in the sample of the first microorganism.

The first and second labels are selected such that the first detectable label provides a first signal, the second detectable label provides a second signal and the first and second detectable labels together yield a third signal that is separately detectable from the first signal and the second signal.

In another embodiment, presented herein is a method for detecting the presence of microorganisms in a sample, comprising:
- (a) contacting the sample with a permeabilizing agent and a plurality of detectably-labeled, microorganism-specific probe sets, wherein said plurality comprises a first probe set specific to a first microorganism comprising a first and second probe, and wherein (i) the first and second probes hybridize to the same nucleic acid sequence, and (ii) the first probe comprises a first detectable label and the second probe comprises a second detectable label; under conditions that allow hybridization of the probes to the nucleic acid sequence of the microorganism; and
- (b) assaying for the presence of the hybridized first probe set, wherein the presence of the hybridized first probe set indicates the presence in the sample of the first microorganism.

In another embodiment, presented herein is a method for detecting the presence of microorganisms in a sample, comprising:
- (a) contacting the sample with a plurality of detectably-labeled, microorganism-specific probe sets, wherein said plurality comprises a first probe set specific to a first microorganism comprising a first and second probe, and wherein (i) the first and second probes hybridize to the same nucleic acid sequence, (ii) the first probe comprises a first detectable label and the second probe comprises a second detectable label, and (iii) the first and second detectable labels are at a fixed ratio; under conditions that allow hybridization of the probes to the nucleic acid sequence of the microorganism; and (b) assaying for the presence of the hybridized first probe set, wherein the presence of the hybridized first probe set indicates the presence in the sample of the first microorganism.

In another embodiment, presented herein is a method for detecting the presence of microorganisms in a sample, comprising:
- (a) contacting the sample with a permeabilizing agent and a plurality of detectably-labeled, microorganism-specific probe sets, wherein said plurality comprises a first probe set specific to a first microorganism comprising a first and second probe, and wherein (i) the first and second probes hybridize to the same nucleic acid sequence, (ii) the first probe comprises a first detectable label and the second probe comprises a second detectable label, and (iii) the first and second detectable labels are at a fixed ratio; under conditions that allow hybridization of the probes to the nucleic acid sequence of the microorganism; and
- (b) assaying for the presence of the hybridized first probe set, wherein the presence of the hybridized first probe set indicates the presence in the sample of the first microorganism.

In another embodiment, presented herein is a method for detecting the presence of microorganisms in a sample, comprising:
- (a) contacting the sample with a plurality of detectably-labeled, microorganism-specific probe sets, wherein said plurality comprises (i) a first probe set specific to a first microorganism, comprising probes labeled with a combination of detectable labels, (ii) a second probe set specific to a second microorganism, comprising probes labeled with a detectable label, and (iii) a third probe set specific to a third microorganism, comprising probes labeled with a detectable label; and wherein the total number of detectable labels in the plurality is less than the total number of different microorganisms that can be detected; under conditions that allow hybridization of the probes to a nucleic acid sequence of a microorganism; and
- (b) assaying for the presence of a hybridized probe set, wherein the presence of a hybridized probe set indicates the presence in the sample of the microorganism for which the probe set is specific.

In another embodiment, presented herein is a method for detecting the presence of microorganisms in a sample, comprising:
- (a) contacting the sample with a permeabilizing agent and a plurality of detectably-labeled, microorganism-specific probe sets, wherein said plurality comprises (i) a first probe set specific to a first microorganism, comprising probes labeled with a combination of detectable labels, (ii) a second probe set specific to a second microorganism, comprising probes labeled with a detectable label, and (iii) a third probe set specific to a third microorganism, comprising probes labeled with a detectable label; and wherein the total number of detectable labels in the plurality is less than the total number of different microorganisms that can be detected; under conditions that allow hybridization of the probes to a nucleic acid sequence of a microorganism; and (b) assaying for the presence of a hybridized probe set, wherein the presence of a hybridized probe set indicates the presence in the sample of the microorganism for which the probe set is specific.

In another embodiment, presented herein is a method for detecting the presence of microorganisms in a sample, comprising:
- (a) contacting the sample with a plurality of detectably-labeled, microorganism-specific probe sets, wherein said plurality comprises (i) a first probe set specific to a first microorganism, comprising probes labeled with a combination of detectable labels at a fixed ratio, (ii) a second probe set specific to a second microorganism, comprising probes labeled with a detectable label, and (iii) a third probe set specific to a third microorganism, comprising probes labeled with a detectable label; and wherein the total number of detectable labels in the plurality is less than the total number of different microorganisms that can be detected; under conditions that allow hybridization of the probes to a nucleic acid sequence of a microorganism; and (b) assaying for the presence of a hybridized probe set, wherein the presence of a hybridized probe set indicates the presence in the sample of the microorganism for which the probe set is specific.

In another embodiment, presented herein is a method for detecting the presence of microorganisms in a sample, comprising:

(a) contacting the sample with a permeabilizing agent and a plurality of detectably-labeled, microorganism-specific probe sets, wherein said plurality comprises (i) a first probe set specific to a first microorganism, comprising probes labeled with a combination of detectable labels at a fixed ratio, (ii) a second probe set specific to a second microorganism, comprising probes labeled with a detectable label, and (iii) a third probe set specific to a third microorganism, comprising probes labeled with a detectable label; and wherein the total number of detectable labels in the plurality is less than the total number of different microorganisms that can be detected; under conditions that allow hybridization of the probes to a nucleic acid sequence of a microorganism; and (b) assaying for the presence of a hybridized probe set, wherein the presence of a hybridized probe set indicates the presence in the sample of the microorganism for which the probe set is specific.

In another embodiment, presented herein is a method for detecting the presence of microorganisms in a sample, comprising:

(a) contacting the sample with a plurality of detectably-labeled, microorganism-specific probe sets, wherein said plurality comprises at least three probe sets, and wherein (i) each probe set is specific to a different microorganism, (ii) the probes in at least one probe set are labeled with a combination of detectable labels, and (iii) the total number of detectable labels in the plurality is less than the total number of different microorganisms that can be detected; under conditions that allow hybridization of the probes to a nucleic acid sequence of a microorganism; and (b) assaying for the presence of a hybridized probe set, wherein the presence of a hybridized probe set indicates the presence in the sample of the microorganism for which the probe set is specific.

In another embodiment, presented herein is a method for detecting the presence of microorganisms in a sample, comprising:

(a) contacting the sample with a plurality of detectably-labeled, microorganism-specific probe sets, wherein said plurality comprises at least three probe sets, and wherein (i) each probe set is specific to a different microorganism, (ii) the probes in at least one probe set are labeled with a combination of detectable labels at a fixed ratio, and (iii) the total number of detectable labels in the plurality is less than the total number of different microorganisms that can be detected; under conditions that allow hybridization of the probes to a nucleic acid sequence of a microorganism; and (b) assaying for the presence of a hybridized probe set, wherein the presence of a hybridized probe set indicates the presence in the sample of the microorganism for which the probe set is specific.

In another embodiment, presented herein is a method for detecting the presence of microorganisms in a sample, comprising:

(a) contacting the sample with a permeabilizing agent and a plurality of detectably-labeled, microorganism-specific probe sets, wherein said plurality comprises at least three probe sets, and wherein (i) each probe set is specific to a different microorganism, (ii) the probes in at least one probe set are labeled with a combination of detectable labels at a fixed ratio, and (iii) the total number of detectable labels in the plurality is less than the total number of different microorganisms that can be detected; under conditions that allow hybridization of the probes to a nucleic acid sequence of a microorganism; and (b) assaying for the presence of a hybridized probe set, wherein the presence of a hybridized probe set indicates the presence in the sample of the microorganism for which the probe set is specific.

In another aspect, methods described herein may be used in conjunction with methods that allow for the characterization of microorganisms in a sample. For example, in certain embodiments, a method described herein may comprise a probe set comprising probes specific to a gene or gene product (e.g., mRNA) of a microorganism that is known to confer resistance to an antimicrobial compound. In other embodiments, a method described herein may comprise a probe set comprising probes specific to a particular type (or Domain) of microorganism, e.g., the method might comprise a probe set that recognizes all members of the Domain Bacteria, but not members of the Archeal or Eukaryotic Domains. Likewise, a probe set may specifically recognize members of Archeal Domain, but not members of the Bacterial or Eukaryotic Domains, and so forth. Probe sets may also be specific to a particular Phylum, Class, Order, Family, Genus, Species, or strain of a microorganism. In other embodiments, a method described herein may comprise one or more DNA staining dyes that stain the DNA of a microorganism.

In another aspect, presented herein are kits for use in determining the presence of microorganisms in a sample. The kits presented herein can be used in accordance with one or more of the methods described herein. Also presented herein are systems for use in determining the presence of microorganisms in a sample. The systems presented herein can use one or more of the kits presented herein.

BRIEF DESCRIPTION OF THE DRAWINGS

FIG. 1 illustrates one embodiment of the present invention that is a multiplex assay for detection of multiple different microorganisms with three different detectable labels for 7 different target microorganisms.

DETAILED DESCRIPTION

Terminology. As used herein, the terms "about" and "approximately," unless otherwise indicated, refer to a value that is no more than 20% above or below the value being modified by the term.

As used herein, the term "detectable label" refers to any label that provides, directly or indirectly, a detectable signal, In some embodiments, a detectable label comprises a biological or chemical molecule, for example, enzymes, radio labeled molecules, fluorescent molecules, fluorophores, particles, chemiluminesors, enzyme substrates or cofactors, enzyme inhibitors, biotin, or magnetic particles. In other embodiments, a detectable label comprises a physical property, e.g., size, shape, electrophoretic mobility, hydrophobicity, hydrophilicity, solubility, and/or chromatographic behavior. In other embodiments, a detectable label comprises an identifier, e.g., a barcode.

As used herein, the term "fluorescent moiety" refers to any compound that emits detectable fluorescence. Examples of fluorescent moieties are well known in the art and include, but are not limited to, coumarins and related dyes, tandem dyes, xanthene dyes (e.g., fluoresceins, rhodols and rhodamines), resorufins, cyanine dyes, bimanes, acridines, isoindoles, dansyl dyes, aminophthalic hydrazides (e.g., luminol and isoluminol derivatives), aminophthalimides, aminobenzofurans, aminoquinolines, dicyanohydroquinones, fluorescent europium, terbium complexes and related compounds. Exemplary fluorescent moieties include FITC, ROX, GFP, Cy5, Cy5.5, Cy3, Cy3B, GFP, YFP, RFP, CFP, Rhodamine Red, Texas Red, Bodipy, IDR700, LightCycler 610, LightCycler 640, LightCycler 670, LightCycler 705, and TAMRA.

As used herein, the terms "growth medium" and "media suitable for growth of a microorganism" are generally related to a nutrient source which allows microorganisms to grow. Growth medium and media suitable for growth of a microorganism may provide vitamins, amino acids, trace elements, salts, compounds and any other substances, whether organic or inorganic, necessary for or conducive to maintain life and foster replication/reproduction of the microorganism. In specific embodiments, growth medium or media suitable for growth of a microorganism is a growth medium that supports the growth of a large number of microorganisms (i.e., a general purpose medium), e.g., a growth medium that is rich in nutrients. In other embodiments, growth medium or media suitable for growth of a microorganism is a growth medium that supports the growth of a specific group of microorganisms (i.e., a selective medium), e.g., microorganisms belonging to a particular family or genus. In yet other embodiments, growth medium or media suitable for growth of a microorganism supports the growth of a single type of microorganism (i.e., a differential medium), e.g., microorganisms belonging to a single species. Those skilled in the art will be able to recognize and select appropriate growth medium based on the type of sample being analyzed using a method described herein and the desired result of the analysis.

As used herein, the terms "hybridize," "hybridizes," and "hybridization" refer to the binding of two or more nucleic acid sequences that are at least 60% (preferably, 70%, 75%, 80%, 85%, 90%, 95%, 98%, 99% or 99.5%) complementary to each other. Nucleic acid hybridization techniques and conditions are known to the skilled artisan and have been described, e.g., in Sambrook et al. Molecular Cloning A Laboratory Manual, 2nd Ed. Cold Spring Lab. Press, (December 1989); U.S. Pat. Nos. 4,563,419 and 4,851,330, and in Dunn, et al., *Cell*, Vol. 12, pp. 23-26 (1978) among many other publications. Various modifications to the hybridization reactions are known in the art including in-solution hybridization or hybridization to capture probes on a solid support in one or more reaction steps.

As used herein, the term "microorganism" generally relates to any microscopic organism, the presence or absence of which is detectable in accordance with the methods described herein. In particular, the microorganisms to be detected include, but are not limited to, bacteria, viruses, yeast, fungi, archae, prokaryotes, protozoa, parasites, and algae. These terms are not mutually exclusive, e.g., many protozoa are parasites and all bacteria are prokaryotes. In accordance with the methods described herein, when a probe set is specific to a first microorganism, a second microorganism, and/or a third microorganism, etc., the microorganisms may represent a single species of microorganism, a particular type of microorganism (e.g., a bacteria or virus). When different microorganisms are detected in accordance with one or more of the methods described herein, the different microorganisms detected may be different species of the same type of microorganism (e.g., different species of bacteria) or may be different types of microorganisms (e.g., a bacteria and/or a yeast are detected).

As used herein, the term "nucleic acid" refers to deoxyribonucleotides, deoxyribonucleic acids, ribonucleotides, and ribonucleic acids, and polymeric forms thereof, and includes either single- or double-stranded forms. Nucleic acids include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleic acid analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), locked-nucleic acids (LNAs), and the like.

As used herein, the term "nucleic acid sequence of a microorganism," similar terms, and variants thereof, refer to a nucleic acid sequence from a microorganism that is accessible to a probe such that the probe can hybridize to the nucleic acid. Such nucleic acid sequences are in a physical and chemical environment that allows the probe to hybridize to it and may be made accessible to the probes by, e.g., permeabilizing the microorganisms using a permeabilizing agent, e.g., saponin, polyethyleneimine, EDTA, lysozyme, or lysostaphin.

As used herein, the term "purified" in the context of nucleic acid molecules refers to a nucleic acid molecule which is separated from other nucleic acid molecules which are present in the natural source of the nucleic acid molecule or to a probe that has been synthesized based on a given nucleic acid sequence and purified from the excess nucleic acids utilized in the synthesis of the probe. In certain embodiments, a purified nucleic acid molecule is at least 60% pure, at least 65% pure, at least 70% pure, at least 75% pure, at least 80% pure, at least 85% pure, at least 90% pure, at least 99% pure, or at least 99.9% pure as assessed by techniques known to one of skill in the art.

As used herein, the term "quencher moiety" refers to a molecule or a part of a compound that is capable of reducing the emission from a fluorescent moiety. Such reduction includes reducing the light after the time when a photon is normally emitted from a fluorescent moiety. Examples of quencher moieties include, but are not limited to, coumarins and related fluorophores, xanthenes (e.g., fluoresceins, rhodols, and rhodamines), resorufins, cyanines, difluoroboradiazindacenes phthalocyanines, DABCYL, and Black Hole Quenchers I-III. Some, but not all, of the quenchers noted above require adequate spectral overlap of the quencher with the fluorescent moiety to result in quenched fluorescence. A variety of molecular mechanisms can result in quenching of fluorescence, and a discussion of various molecular quenching mechanisms is given by Lakowicz in *Principles of Fluorescence Spectroscopy*, (Second Edition) pp 238-258 (publisher: Kluwer Academic/Plenum Publisher (1999)).

As used herein, the term "quenching" refers to partial or full suppression of fluorescence from a fluorescent moiety by a quencher moiety. The quenching phenomena may occur between two fluorescent components that are the same or substantially the same (e.g., a single cyanine dye) or two fluorescent components that are different (e.g., a cyanine dye and a squaraine dye), or between a fluorescent component (e.g., fluorescein) and a non-fluorescent component (e.g., DABCYL).

As used herein, the term "sample," refers to anything that can be isolated from, obtained from, derived from, or taken from any source that is used in accordance with one or more of the methods described herein. In certain embodiments, a sample allows for any nucleic acid sequence of a microorganism to be accessible to probes for hybridization.

As used herein, the term "source" refers to anything which can provide a sample that can be used in one or more of the methods described herein. Sources may include, but are not limited to, any living subject, (e.g., a human or non-human animal), an element of nature (e.g., water or soil), a beverage (e.g., milk), a food product (e.g., meat or poultry), a cosmetic composition/formulation, or a pharmaceutical composition/formulation.

As used herein, the terms "subject" and "patient" are used interchangeably to refer to an animal subject. In one embodiment, the subject is a mammal. In another embodiment, the subject is a non-human animal. In another embodiment, the subject is a human.

Described herein are methods for the rapid detection of the presence or absence of one or more microorganisms in a sample using selected combinations of detectably-labeled probes. In some embodiments, the methods presented herein utilize probes labeled with combinations of detectable labels, so as to allow for the detection of multiple microorganisms in a sample using a minimum number of detectably-labeled probes, i.e., the total number of detectable labels used in the method is less than the total number of different microorganisms that can be detected in the sample by the method. Certain methods presented herein take advantage of the fact that detectable labels can be combined in different combinations and at different ratios, such that a given combination or ratio of detectable labels can be specific for one microorganism whereas a different combination or ratio of the same detectable labels can be specific for another microorganism. Such methods allow for the detection of a wide-range of different microorganisms while only requiring the detection of a limited number of detectable labels.

In algorithmic terms the present invention contemplates detecting N microorganisms using fewer than N (i.e. N−1 or less) different labels. Each microorganism is detected by a probe set that hybridizes to the nucleic acid of a specific one of the N microorganisms. Each probe set has at least one detectably labeled probe. The detectable labels selected for each probe set are either one or more than one, depending upon the desired signal indicating the presence of the one of N microorganisms. Examples of detectable labels include dyes. Table 1 depicts examples of these dye combinations and the formula used in determining how many organisms can be detected based on a given dye/probe combination.

TABLE 1

Potential Dye Combinations and Level of Multiplexing Possible for Combinatorial FISH

| Number of Dyes (Fluorescence Channels), N | Maximum Combinations Possible* | Examples of Potentially Compatible Dye Combinations | Examples of Commercial Flow Cytometers possessing required number of fluorescence channels |
|---|---|---|---|
| 1 | 1 | any | any |
| 2 | 3 | FITC, ROX | FACSAria ™/FACSCalibur ™ |
| 3 | 7 | FITC, ROX, Cy5 | FACSAria ™/FACSCalibur ™ |
| 4 | 15 | FITC, Cy3, ROX, Cy5 | FACSCalibur ™ |
| 5 | 31 | FITC, Cy3, ROX, Cy5, Cy5.5 | FACSCanto ™ |
| 6 | 63 | HTC, Cy3, ROX, LightCycler 640, Cy5, Cy5.5 | FACSCanto ™ |

*Maximum number of combinations (i.e. level of multiplexing) possible for N colors is $$\sum_{r=1}^{N} N!/r!(N-r)!$$

assuming one ratio per dye combination

For example, a method described herein may comprise three probe sets that comprise detectably labeled probes, wherein the probes in the first probe set are specific to a first microorganism and comprise fluorescent red detectable labels, the probes in the second probe set are specific to a second microorganism and comprise fluorescent green detectable labels, and the probes in the third probe set are specific to a third microorganism and comprise a combination of fluorescent red and fluorescent green detectable labels. In accordance with this example, three different microorganisms can be detected using just two detectable labels, i.e., fluorescent red and fluorescent green detectable labels. In this example the presence of the first microorganism is indicated by the fluorescent green, the presence of the second microorganism is indicated by the fluorescent red and the third microorganism is indicated by the green/red combination.

The "Maximum Possible Combinations" shown in Table 1 are calculated from the summed factorial expression shown below the table. This calculation determines the maximum number of possible dye combinations for the simplest case in which each dye combination is represented once. The calculation does not include possible variations in the relative amounts (ratio) of one dye versus another for a particular combination. Specifically, it does not account for the possibility of additional combinations produced by varying the relative amounts of dyes between different probe sets for a given combination. For example, five combinations (rather than the three shown in Table 1) are possible for the FITC, ROX dye pair if the ratio of FITC and ROX are varied between probe sets as follows: Probe set 1(FITC only), Probe set 2 (ROX only), Probe Set 3 (FITC:ROX ratio=1:1), Probe Set 4 (FITC:ROX-1:2), Probe Set 5 (FITC:ROX=2:1). Similarly, by varying the ratios of the detectable labels between probe sets, of any of the dye combinations shown in Table 1, a larger number of combinations is possible than stated in Table 1.

Examples of potentially compatible dye combinations shown in Table 1 were chosen with the objective of maximizing the spectral separation of fluorescence emission profiles of the various dyes to allow independent measurement of each dye by use of selective optical filters. The wavelengths for maximum fluorescence emission of the dyes shown in Table 1 are as follows: FITC (520 nm), Cy3 (570 nm), ROX (605 nm), LightCycler-640 (640 nm), Cy5 (667 nm), Cy5.5

(694 nm). The invention contemplates other combinations of dyes with acceptable spectral separation.

FIG. 1 presents an example of how a method described herein could be used to detect a wide-range of different microorganisms while only requiring the detection of a limited number of detectable labels. As seen in FIG. 1, by using various combinations of the same three detectable labels (i.e., a detectable label with red fluorescence, a detectable label with green fluorescence, and a detectable label with blue fluorescence), seven different microorganisms can be identified. By using these three detectable labels at different ratios to one another for each microorganism in accordance with certain methods described herein, then the number of microorganisms that could be detected would greatly exceed seven.

Methods described herein may be used in conjunction with methods that allow for the characterization of microorganisms in a sample. For example, in certain embodiments, a method described herein may comprise a probe set comprising probes specific to a gene or gene product (e.g., mRNA) of a microorganism that is known to confer resistance to an antimicrobial compound. In other embodiments, a method described herein may comprise a probe set comprising probes specific to a particular type (or Domain) of microorganism, e.g., the method might comprise a probe set that recognizes all members of the Domain Bacteria, but not members of the Archeal or Eukaryotic Domains. Likewise, a probe set may specifically recognize members of Archeal Domain, but not members of the Bacterial or Eukaryotic Domains, and so forth. Probe sets may also be specific to a particular Phylum, Class, Order, Family, Genus, Species, or strain of a microorganism. In other embodiments, a method described herein may comprise one or more DNA staining dyes that stain the DNA of a microorganism.

Methods For Detecting Microorganisms. In one embodiment, presented herein is a method for detecting the presence of microorganisms in a sample, comprising:
(a) contacting the sample with a plurality of detectably-labeled, microorganism-specific probes, wherein said plurality comprises a first probe set comprising a first probe that is specific to a first microorganism, and wherein each first probe in the first probe set comprises a first detectable label and a second detectable label; under conditions that allow hybridization of the probes to a nucleic acid sequence of the first microorganism; and
(b) assaying for the presence of the hybridized first probes, wherein the presence of the hybridized first probes indicates the presence in the sample of the first microorganism.

In one aspect, the plurality of detectably labeled, microorganism specific probe sets comprises a second probe set specific to a second microorganism. In another aspect, the plurality of delectably labeled, microorganism specific probe sets comprises a second probe set specific to a second microorganism and a third probe set specific to a third microorganism, wherein the total number of detectable labels in the plurality is less than the total number of different microorganisms that can be detected. In another aspect, the plurality of detectably labeled, microorganism specific probe sets comprises a second probe set specific to a second microorganism, a third probe set specific to a third microorganism, and a fourth probe set specific to a fourth microorganism, wherein the total number of detectable labels in the plurality is less than the total number of different microorganisms that can be detected. In another aspect, the plurality of detectably labeled, microorganism specific probe sets comprises at least five probe sets, wherein each probe set is specific to a different microorganism, wherein the total number of detectable labels in the plurality is less than the total number of different microorganisms that can be detected. In another aspect, the sample is contacted with a permeabilizing agent concurrently with or prior to step (a).

In another embodiment, presented herein is a method for detecting the presence of microorganisms in a sample, comprising:
(a) contacting the sample with a plurality of detectably-labeled, microorganism-specific probes, wherein said plurality comprises a first probe set comprising a first probe that is specific to a first microorganism, and wherein (i) each first probe in the first probe set comprises a first detectable label and a second detectable label and (ii) the first and second detectable labels are at a fixed ratio; under conditions that allow hybridization of the probes to a nucleic acid sequence of the first microorganism; and
(b) assaying for the presence of the hybridized first probe set, wherein the presence of the hybridized first probe set indicates the presence in the sample of the first microorganism.

In one aspect, the plurality of detectably labeled, microorganism specific probe sets comprises a second probe set specific to a second microorganism, wherein each probe in the second probe set comprises the first detectable label and the second detectable label at a different fixed ratio than the first probe set. In another aspect the plurality of detectably labeled, microorganism-specific probe sets comprises a second probe set specific to a second microorganism and a third probe set specific to a third microorganism, wherein each probe in the second and third probe sets comprises the first and second detectable label, and wherein the first and second detectable labels in the first, second, and third probe sets are at different fixed ratios. In another aspect, the sample is contacted with a permeabilizing agent concurrently with or prior to step (a).

In another embodiment, presented herein is a method for detecting the presence of microorganisms in a sample, comprising:
(a) contacting the sample with a plurality of detectably-labeled, microorganism-specific probe sets, wherein said plurality comprises a first probe set specific to a first microorganism comprising a first and second probe, and wherein (i) the first and second probes hybridize to the same nucleic acid sequence, and (ii) the first probe comprises a first detectable label and the second probe comprises a second detectable label; under conditions that allow hybridization of the probes to the nucleic acid sequence of the microorganism; and
(b) assaying for the presence of the hybridized first probe set, wherein the presence of the hybridized first probe set indicates the presence in the sample of the first microorganism.

In one aspect, the plurality of detectably labeled, microorganism specific probe sets comprises a second probe set specific to a second microorganism. In another aspect, the plurality of detectably labeled, microorganism specific probe sets comprises a second probe set specific to a second microorganism and a third probe set specific to a third microorganism, wherein the total number of detectable labels in the plurality is less than the total number of different microorganisms that can be detected. In another aspect, the plurality of detectably labeled, microorganism specific probe sets comprises a second probe set specific to a second microorganism, a third probe set specific to a third microorganism, and a fourth probe set specific to a fourth microorganism, wherein the total number of detectable labels in the plurality is less than the total number of different microorganisms that can be detected. In another aspect, the plurality of detectably labeled, microorganism specific probe sets comprises at least five probe sets, wherein each probe set is specific to a different microorganism, wherein the total number of detectable labels in the plurality is less than the total number of different microorganisms that can be detected. In another aspect, the sample is contacted with a permeabilizing agent concurrently with or prior to step (a).

In another embodiment, presented herein is a method for detecting the presence of microorganisms in a sample, comprising:
  (a) contacting the sample with a plurality of detectably-labeled, microorganism-specific probe sets, wherein said plurality comprises a first probe set specific to a first microorganism comprising a first and second probe, and wherein (i) the first and second probes hybridize to the same nucleic acid sequence, (ii) the first probe comprises a first detectable label and the second probe comprises a second detectable label, and (iii) the first and second detectable labels are at a fixed ratio; under conditions that allow hybridization of the probes to the nucleic acid sequence of the microorganism; and
  (b) assaying for the presence of the hybridized first probe set, wherein the presence of the hybridized first probe set indicates the presence in the sample of the first microorganism.

In one aspect, the plurality of detectably labeled, microorganism specific probe sets comprises a second probe set specific to a second microorganism comprising a first and second probe, wherein the first and second probes hybridize to the same nucleic acid sequence of the second microorganism, and wherein (i) the first probe comprises the first detectable label and the second probe comprises the second detectable label and (ii) the first and second detectable labels in the second probe set are at a different fixed ratio than the first and second detectable labels in the first probe set. In another aspect, the plurality of detectably labeled, microorganism specific probe sets comprises a second probe set specific to a second microorganism and a third probe set specific to a third microorganism, wherein (i) the second and third probe sets comprise a first and second probe, (ii) the first and second probes of the second and third probe sets hybridize to the same nucleic acid sequence of the second and third microorganism, respectively, (iii) the first probe in the second and third probe sets comprises the first detectable label and the second probe in the second and third probe sets comprises the second detectable label, and (iv) the first and second detectable labels in the first, second, and third probe sets are at different fixed ratios. In another aspect, the sample is contacted with a permeabilizing agent concurrently with or prior to step (a).

In another embodiment, presented herein is a method for detecting the presence of microorganisms in a sample, comprising:
  (a) contacting the sample with a plurality of detectably-labeled, microorganism-specific probe sets, wherein said plurality comprises (i) a first probe set specific to a first microorganism, comprising probes labeled with a combination of detectable labels, (ii) a second probe set specific to a second microorganism, comprising probes labeled with a detectable label, and (iii) a third probe set specific to a third microorganism, comprising probes labeled with a detectable label; and wherein the total number of detectable labels in the plurality is less than the total number of different microorganisms that can be detected; under conditions that allow hybridization of the probes to a nucleic acid sequence of a microorganism; and
  (b) assaying for the presence of a hybridized probe set, wherein the presence of a hybridized probe set indicates the presence in the sample of the microorganism for which the probe set is specific.

In one aspect, the probes in the first, second, and third probe sets are complementary to a single nucleic acid sequence of the first microorganism, the second microorganism, and the third microorganism, respectively. In another aspect, the probes in the first, second, and third probe sets are complementary to more than one nucleic acid sequence of the first microorganism, the second microorganism, and the third microorganism, respectively. In another aspect, the plurality of detectably labeled, microorganism specific probe sets comprises a fourth probe set specific to a fourth microorganism and a fifth probe set specific to a fifth microorganism. In another aspect, the plurality of detectably labeled, microorganism specific probe sets comprises a fourth probe set specific to a fourth microorganism, a fifth probe set specific to a fifth microorganism, and a sixth probe set specific to a sixth microorganism. In another aspect, the plurality of detectably labeled, microorganism specific probe sets comprises a fourth probe set specific to a fourth microorganism, a fifth probe set specific to a fifth microorganism, a sixth probe set specific to a sixth microorganism, and a seventh probe set specific to a seventh microorganism. In another aspect, the probes in the fourth, fifth, sixth, and/or seventh probe sets are labeled with a combination of detectable labels at a fixed ratio, wherein the fixed ratios are different between the probes in the different probe sets. In another aspect, the sample is contacted with a permeabilizing agent concurrently with or prior to step (a).

In another embodiment, presented herein is a method for detecting the presence of microorganisms in a sample, comprising:
  (a) contacting the sample with a plurality of detectably-labeled, microorganism-specific probe sets, wherein said plurality comprises (i) a first probe set specific to a first microorganism, comprising probes labeled with a combination of detectable labels at a fixed ratio, (ii) a second probe set specific to a second microorganism, comprising probes labeled with a detectable label, and (iii) a third probe set specific to a third microorganism, comprising probes labeled with a detectable label; and wherein the total number of detectable labels in the plurality is less than the total number of different microorganisms that can be detected; under conditions that allow hybridization of the probes to a nucleic acid sequence of a microorganism; and
  (b) assaying for the presence of a hybridized probe set, wherein the presence of a hybridized probe set indicates the presence in the sample of the microorganism for which the probe set is specific.

In one aspect, the probes in the first, second, and third probe sets are complementary to a single nucleic acid sequence of the first microorganism, the second microorganism, and the third microorganism, respectively. In another aspect, the probes in the first, second, and third probe sets are complementary to more than one nucleic acid sequence of the first microorganism, the second microorganism, and the third microorganism, respectively. In another aspect, the plurality of detectably labeled, microorganism specific probe sets comprises a fourth probe set specific to a fourth microorganism. In another aspect, the plurality of detectably labeled, microorganism specific probe sets comprises a fourth probe set specific to a fourth microorganism and a fifth probe set specific to a fifth microorganism. In another aspect, the plurality of detectably labeled, microorganism specific probe sets comprises a fourth probe set specific to a fourth microorganism, a fifth probe set specific to a fifth microorganism, and a sixth probe set specific to a sixth microorganism. In another aspect, the plurality of detectably labeled, microorganism specific probe sets comprises a fourth probe set specific to a fourth microorganism, a fifth probe set specific to a fifth microorganism, a sixth probe set specific to a sixth microorganism, and a seventh probe set specific to a seventh microorganism. In another aspect, the probes in the fourth, fifth, sixth, and/or seventh probe sets are labeled with a combination of detectable labels at a fixed ratio, wherein the fixed ratios are different between the probes in the different probe sets. In another aspect, the sample is contacted with a permeabilizing agent concurrently with or prior to step (a).

In another embodiment, presented herein is a method for detecting the presence of microorganisms in a sample, comprising:
 (a) contacting the sample with a plurality of detectably-labeled, microorganism-specific probe sets, wherein said plurality comprises at least three probe sets, and wherein (i) each probe set is specific to a different microorganism, (ii) the probes in at least one probe set are labeled with a combination of detectable labels, and (iii) the total number of detectable labels in the plurality is less than the total number of different microorganisms that can be detected; under conditions that allow hybridization of the probes to a nucleic acid sequence of a microorganism; and
 (b) assaying for the presence of a hybridized probe set, wherein the presence of a hybridized probe set indicates the presence in the sample of the microorganism for which the probe set is specific.

In one aspect, the probes in the first, second, and third probe sets are complementary to a single nucleic acid sequence of the first microorganism, the second microorganism, and the third sets are complementary to more than one nucleic acid sequence of the first microorganism, the second microorganism, and the third microorganism, respectively. In another aspect, the plurality of detectably labeled, microorganism specific probe sets comprises a fourth probe set specific to a fourth microorganism. In another aspect, the plurality of detectably labeled, microorganism specific probe sets comprises a fourth probe set specific to a fourth microorganism and a fifth probe set specific to a fifth microorganism. In another aspect, the plurality of detectably labeled, microorganism specific probe sets comprises a fourth probe set specific to a fourth microorganism, a fifth probe set specific to a fifth microorganism, and a sixth probe set specific to a sixth microorganism. In another aspect, the plurality of detectably labeled, microorganism specific probe sets comprises a fourth probe set specific to a fourth microorganism, a fifth probe set specific to a fifth microorganism, a sixth probe set specific to a sixth microorganism, and a seventh probe set specific to a seventh microorganism. In another aspect, the probes in the fourth, fifth, sixth, and/or seventh probe sets are labeled with a combination of detectable labels at a fixed ratio, wherein the fixed ratios are different between the probes in the different probe sets. In another aspect, the sample is contacted with a permeabilizing agent concurrently with or prior to step (a).

In another embodiment, presented herein is a method for detecting the presence of microorganisms in a sample, comprising:
 (a) contacting the sample with a plurality of detectably-labeled, microorganism-specific probe sets, wherein said plurality comprises at least three probe sets, and wherein (i) each probe set is specific to a different microorganism, (ii) the probes in at least one probe set are labeled with a combination of detectable labels at a fixed ratio, and (iii) the total number of detectable labels in the plurality is less than the total number of different microorganisms that can be detected; under conditions that allow hybridization of the probes to a nucleic acid sequence of a microorganism; and
 (b) assaying for the presence of a hybridized probe set, wherein the presence of a hybridized probe set indicates the presence in the sample of the microorganism for which the probe set is specific.

In one aspect, the probes in the first, second, and third probe sets are complementary to a single nucleic acid sequence of the first microorganism, the second microorganism, and the third microorganism, respectively. In another aspect, the probes in the first, second, and third probe sets are complementary to more than one nucleic acid sequence of the first microorganism, the second microorganism, and the third microorganism, respectively. In another aspect, the plurality of detectably labeled, microorganism specific probe sets comprises a fourth probe set specific to a fourth microorganism. In another aspect, the plurality of detectably labeled, microorganism specific probe sets comprises a fourth probe set specific to a fourth microorganism and a fifth probe set specific to a fifth microorganism. In another aspect, the plurality of detectably labeled, microorganism specific probe sets comprises a fourth probe set specific to a fourth microorganism, a fifth probe set specific to a fifth microorganism, and a sixth probe set specific to a sixth microorganism. In another aspect, the plurality of detectably labeled, microorganism specific probe sets comprises a fourth probe set specific to a fourth microorganism, a fifth probe set specific to a fifth microorganism, a sixth probe set specific to a sixth microorganism, and a seventh probe set specific to a seventh microorganism. In another aspect, the probes in the fourth, fifth, sixth, and/or seventh probe sets are labeled with a combination of detectable labels at a fixed ratio, wherein the fixed ratios are different between the probes in the different probe sets. In another aspect, the sample is contacted with a permeabilizing agent concurrently with or prior to step (a).

Probes. A probe can refer to any nucleic acid sequence that is designed to specifically hybridize to a target nucleic acid sequence of interest. Typically, but not exclusively, a probe is associated with a detectable label so that the probe (and therefore its nucleic acid target) can be detected, visualized, measured and/or quantified.

The probes used in accordance with the methods described herein can be based on, derived from, or consist of any probes known in the art or can be developed based on any microorganism nucleic acid sequence known or determined, or an analog thereof.

In certain embodiments, the probes used in accordance with the methods described herein may comprise DNA or RNA oligonucleotides and may be chemically synthesized using techniques known in the art. In a specific embodiment, the probes used in accordance with the methods described herein are peptide-nucleic acid (PNA) probes. PNAs are well known by those of skill in the art (see, e.g., Egholm et al., *Nature*, 365:566-568 (1993)). In another specific embodiment, the probes used in accordance with the methods described herein are locked nucleic acid (LNA) probes. LNAs are well known by those of skill in the art (see, e.g., Koshkin et al., *J. Am. Chem. Soc.*, 120:13252-13253 (1998)).

Probes of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. The probes encompassed here exhibit specificity, under hybridization conditions, for a nucleic acid sequence of a microorganism in a sample, and can be designed to hybridize to deoxyribonucleic acid (DNA) or ribonucleic acid (RNA) e.g., ribosomal RNA (rRNA) or messenger RNA (mRNA). In specific embodiments, when the nucleic acid sequence of the microorganism is not from a virus, the probes used in accordance with the methods described herein bind to rRNA. Ribosomal RNA sequences are relatively abundant in cells and rRNA contains regions of sequence variability that can be exploited to design probes capable of distinguishing between closely related organisms. Viral nucleic acid sequences, which do not contain rRNA, can be detected by targeting DNA, RNA, or a messenger RNA (mRNA) sequence.

The probes used in accordance with the methods described herein may hybridize to a nucleic acid sequence of a microorganism of any length so long as hybridization takes place. For example, a probe may hybridize to a nucleic acid sequence of a microorganism that is between 5 to 15 bases in length, 5 to 25 bases in length, 5 to 50 bases in length, 5 to 100 bases in length, 5 to 250 bases in length, 5 to 500 bases in length, 5 to 1000 bases in length, 20 to 25 bases in length, 20 to 50 bases in length, 20 to 100 bases in length, 20 to 250 bases in length, 20 to 500 bases in length, or 20 to 1000 bases in length. In some embodiments, the nucleic acid sequence of a microorganism comprises additional nucleic acids to which the probe does not hybridize. In other embodiments, the nucleic acid sequence of a microorganism does not comprise additional nucleic acids to which the probe does not hybridize.

In certain embodiments, the probes used in accordance with the methods described herein hybridize to their complementary nucleic acid sequences under high stringency, intermediate or lower stringency hybridization conditions, wherein the choice of hybridization conditions used determines the degree of stringency of hybridization. Optimal hybridization conditions will depend on the length and type (e.g., RNA, or DNA) of probe and nucleic acid to which the probe hybridizes. Those of skill in the art will appreciate that as probes become shorter, it may become necessary to adjust their length to achieve a relatively uniform melting temperature for satisfactory hybridization results. General parameters for stringent hybridization conditions for nucleic acids are described in Sambrook et al., *MOLECULAR CLONING-A LABORATORY MANUAL* (2nd Ed.), Vols. 1-3, Cold Spring Harbor Laboratory, Cold Spring Harbor, N.Y. (1989), and in Ausubel et al., *CURRENT PROTOCOLS IN MOLECULAR BIOLOGY*, Vol. 2, Current Protocols Publishing, New York (1994).

A probe used in accordance with the methods described herein may include one or more nucleic acid sequences in addition to the nucleic acid sequence of the microorganism which do not hybridize to the nucleic acid sequence of the microorganism. An additional nucleic acid sequence might be a 5' sequence recognized by a RNA polymerase or which enhances initiation or elongation by an RNA polymerase (e.g., a T7 promoter). More than one additional nucleic acid sequence may be included if the first sequence is incorporated into, for example, a self-hybridizing probe (i.e., a probe having distinct base regions capable of hybridizing to each other in the absence of a complementary nucleic acid sequence of a microorganism under the conditions of an assay). Self-hybridizing probes may be used in accordance with any of the methods described herein. In certain embodiments, self-hybridizing probes comprise one or more detectable labels. In specific embodiments, self-hybridizing probes comprise a fluorescent moiety and a quencher moiety.

The probes used in accordance with the methods described herein may hybridize to their complementary nucleic acid sequences with varying degrees of specificity. In certain embodiments, the probes hybridize with nucleic acid sequences that are 100% complementary to that of the probe. In other embodiments, the probes hybridize with nucleic acid sequences that are greater than 90% complementary to that of the probe. In other embodiments, the probes hybridize with nucleic acid sequence that are greater than 85% complementary to that of the probe. In other embodiments, the probes hybridize with nucleic acid sequences that are greater than 80% complementary to that of the probe. In other embodiments, the probes hybridize with nucleic acid sequences that are greater than 75% complementary to that of the probe. In other embodiments, the probes hybridize with nucleic acid sequences that are greater than 70% complementary to that of the probe. In other embodiments, the probes hybridize with nucleic acid sequences that are greater than 60% complementary to that of the probe. In certain embodiments, the probes hybridize with nucleic acid sequences that are 60% to 100%, 70% to 100%, 75% to 100%, 80% to 100%, 85% to 100%, 90% to 100%, or 95% to 100% complementary to that of the probe.

The probes used in accordance with the methods described herein can be designed to be specific to a single species of microorganism, a single strain of microorganism, a class of microorganisms, or a family or microorganisms. Exemplary microorganism-specific probes are well-known in the art (see, e.g., Kempf et al., *J. Clin. Microbiol.* 38:830-838 (2000)). Alternatively, the probes used in accordance with the methods described herein can be "universal" probes or "pan" probes. Such probes hybridize to the nucleic acid sequences of a plurality of microorganisms, i.e., the probes can be designed to be specific to many different genuses of microorganisms, a single genus of microorganisms, a family of microorganisms, etc. For example, the highly conserved 16S ribosomal RNA-coding sequences contain regions that are found in bacteria, or groupings of bacteria (e.g., Eubacteria, Gram-positive bacteria or Gram-negative bacteria), but are not in humans and other higher organisms, and thus probes may be designed and used in the methods provided herein that bind to a plurality of such microorganisms. See, e.g., McCabe et al., *Molecular Genetics and Metabolism*, Vol. 66, pp. 205-211 (1999); Schmidt, T. et al., *Meth. Enzymol.*, Vol. 235, pp. 205-222 (1994) (method for identifying pathogens); Kunishima, S. et al., *Transfusion*, Vol. 40, p. 1420 (2000) (method for detecting bacteria in blood); Greisen, K., *J. Clin. Microbiol.*, Vol. 32, pp. 335-351 (1994) (method for detecting pathogenic bacteria in cerebral spinal fluid); Jordan, J., *J. Mol. Diag.*, Vol. 7, pp. 575-581 (2005) (method for diagnosing sepsis in neonates); Rothman, R., et al., *J. Infect. Dis.*, Vol. 186, pp. 1677-1681 (2002) (method for diagnosing acute bacterial endocarditis); and Cox, C., et al, *Arthritis Res. Ther.*, Vol. 5, pp. R1-R8 (2002) (detecting bacteria in synovial fluid). Similarly, universal probes for other microorganisms, such as fungi, have been described. See, e.g., Maaroati, V. et al. (2003) *J. Clin. Microbiol.*, Vol. 41, 3293-3298 (method for quantifying *Candida albicans* in blood); Can, M. et al., *J. Clin. Microbiol.* Vol. 43, pp. 3023-3026 (2005) (method for detecting *Candida dubliniensis* in blood); and White, P. et al., *J. Med. Microbiol.* Vol. 52, pp. 229-238 (2003) (method for detecting systemic fungal infections). Any universal probes known or developed for a given class of microorganism may be used in accordance with the methods described herein.

The probes used in accordance with the methods described herein can be used at any concentration or amount, so long as the concentration or amount of probe used is sufficient to achieve the desired result of the method. In certain embodiments, the amount of probe used is about 0.001 µg about 0.01 µg, about 0.1 µg, about 1.0 µg, or more than 1.0 µg. To achieve desired concentrations of probes, the probe scan be suspended in a buffer suitable for use in the methods described herein. Exemplary concentrations of probes used herein include 0.0001 µg/ml of probe, 0.001 µg/ml of probe, 0.01 µg/ml of probe, 0.1 µg/ml of probe, 1.0 µg/ml of probe, and 10.0 µg/ml of probe.

In certain embodiments, the probes used in accordance with the methods described herein comprise a detectable label. In certain embodiments, a detectable label refers to a moiety, such as a luminescent moiety, a fluorescent moiety, or radioactive isotope or group containing the same, and nonisotopic labels, such as enzymes or dyes. In other embodiments, a detectable refers to a moiety that can be used indirectly to achieve detection, e.g., biotin. The probes may be labeled with a detectable label either directly or indirectly. Indirect labeling methods are well known in the art (see, generally, *Current Protocols in Immunology*, pp. 8.10.12, -8.10.21 (Coligan et al., eds. John Wiley & Sons, Inc., pub.) (1997). Direct methods for linking detectable labels to probes are well known to those of skill in the art. For example, European Patent Publication No. EP 0370 694 A2, entitled, "Diagnostic Kit and Method Using a Solid Phase Capture Means For Detecting Nucleic Acid", to Burdick and Oakes, which was published on May 30, describes methods of linking labels to probes. For example, direct labeling can be accomplished by incorporating fluorescent dye-labeled phosphoramidites into a probe during synthesis. Fluorescently labeled nucleoside analogs are available commercially, or can be produced synthetically, by methods known in the art (see, Brumbaugh et al., *Proc. Natl. Acad. Sci.* (USA), Vol. 85, pp. 5610-5614 (1988)). These references are incorporated by reference herein.

In certain embodiments, wherein the probes used in accordance with the methods described herein comprise a fluorescent moiety, the fluorescent signal that is emitted from the probe in the presence of a complementary nucleic acid sequence of a microorganism is at least about 5%, 10%, 20%, 30%, 40%, 50%, 60%, 70%, 80%, 90%, or 100% higher than the fluorescent signal that is emitted from the probe in the absence of the complementary nucleic acid sequence of a microorganism. In other embodiments, the fluorescent signal that is emitted from the probe in the presence of the complementary nucleic acid sequence of a microorganism is at least about 1 fold, 1.5 fold, 2 fold, 3 fold, 4 fold, 5 fold, 10 fold, 15 fold, 20 fold, 50 fold, 100 fold, 500 fold, or 1,000 fold higher than the fluorescent signal that is emitted from the probe in the absence of the complementary nucleic acid sequence of a microorganism. In other specific embodiments, the signal to noise ratio (S:N) measured from the binding of a probe to its complementary nucleic acid sequence of a microorganism is at least about 1 fold, 1.5 fold, 2 fold, 3 fold, 4 fold, 5 fold, 10 fold, 15 fold, 20 fold, 50 fold, 100 fold, 500 fold, or 1,000 fold higher than the S:N that is measured from the binding of the probe to a nucleic acid sequence that is not complementary to the nucleic acid sequence of the probe in other specific embodiments, the signal to noise ratio (S:N) measured from the binding of a probe to its complementary nucleic acid sequence of a microorganism is at least about 5%, 10%, 20%, 30%, 40%, 50%, 60%, 70%, 80%, 90%, 100%, 500%, 1000%, or greater than 1000% higher than the S:N that is measured from the binding of the probe to a nucleic acid sequence that is not complementary to the nucleic acid sequence of the probe. In other specific embodiments, the mean fluorescence intensity (MFI) that is measured from the binding of a probe to its complementary nucleic acid sequence of a microorganism is at least about 1 fold, 1.5 fold, 2 fold, 3 fold, 4 fold, 5 fold, 10 fold, 15 fold, 20 fold, 50 fold, 100 fold, 500 fold, or 1,000 fold higher than the MFI that is measured from the binding of the probe to a nucleic acid sequence that is not complementary to the nucleic acid sequence of the probe. In other specific embodiments, the mean fluorescence intensity (MFI) that is measured from the binding of a probe to its complementary nucleic acid sequence of a microorganism is at least about 5%, 10%, 20%, 30%, 40%, 50%, 60%, 70%, 80%, 90%, 100%, 500%, 1000%, or greater than 1000% higher than the MR that is measured from the binding of the probe to a nucleic acid sequence that is not complementary to the nucleic acid sequence of the probe.

In one exemplary embodiment, a probe can be labeled with a single detectable label. In other embodiments, a probe can be labeled with more than one detectable label. In specific embodiments, a probe can be labeled with more than one detectable label, wherein the more than one detectable label can comprise the same detectable label (e.g., the probe is labeled with two or more molecules of green fluorescent protein (GFP)) or the more than one detectable label can comprise two or more distinct detectable labels (e.g., the probe is labeled with one or more molecules of GFP and one or more molecules of red fluorescent protein (RFP)). In certain embodiments, when a probe is labeled with two or more distinct detectable labels, the two or more distinct detectable labels may be at a fixed ratio to one another (e.g., the probe is labeled with two molecules of GFP and one molecule of RFP, making the ratio of GFP to RFP a 2:1 ratio). Probes comprising detectable labels at fixed ratios are described in greater detail herein. Moreover, those of skill in the art will recognize how probes can be labeled with various numbers of different detectable labels as a means to generate detectable labels at the desired fixed ratios. Methods for labeling probes with detectable labels, e.g., fluorescent moieties, are well-known in the art (see, e.g., U.S. Pat. Nos. 6,472,156, 6,451,543, 6,348,322, 6,342,379, 6,323,039 6,297,018, 6,291,201, 6,280,981, 5,843,658 and 5,439,797 which are incorporated by reference herein).

In one embodiment, a probe may comprise a fluorescent moiety and a quencher moiety positioned in the probe so that the quencher and fluorescent moiety are brought together in the absence of a complementary nucleic acid sequence of a microorganism. For example, the fluorescent moiety may be positioned at one terminus of a probe and the quencher moiety may be positioned at the other terminus of the probe, wherein the probe adopts one conformation or secondary structure, such as a stem-loop or hairpin loop, when not bound or hybridized to a complementary nucleic acid sequence of a microorganism, and adopts a different conformation or secondary structure when bound or hybridized to a complementary nucleic acid sequence of a microorganism. For example, upon binding between the probe and the complementary nucleic acid sequence of a microorganism, the quencher moiety and fluorescent moiety separate, resulting in dequenching of the fluorescent signal emitted by the fluorescent moiety. In certain embodiments, a probe comprises both a fluorescent moiety and quencher moiety such that the fluorescent moiety and quencher moiety are at most 0.5 nm, at most 1 nm, at most 5 nm, at most 10 nm, at most 15 nm, or at most 20 nm apart from each other, In other embodiments, the distance between a quencher moiety and the fluorescent moiety on a probe is about 10, 15, 20, 30, 40, 50, 60, 70, 80, 90, 100, 105, 110, 115, 120, 130, 140, or 150 Å, or any value in between. In other embodiments, a probe comprises both a fluorescent moiety and a quencher moiety such that the fluorescent moiety and quencher moiety are at least 2, at least 3, at least 4, at least 5, at least 6, at least 7, at least 8, at least 9, at least 10, at least 15, at least 20, at least 50, at least 100, or at least 200 nucleotides apart from one another. In other embodiments, a probe comprises both a fluorescent moiety and a quencher moiety such that the fluorescent moiety and quencher moiety are at least 2 to 5, 2 to 10, 2 to 15, 2 to 20, 3 to 5, 3 to 10, 3 to 15, 3 to 20, 5 to 10, 5 to 20, 5 to 50, 5 to 100, 5 to 200, 10 to 20, 10 to 50, 10 to 100, 10 to 200, 10 to 300, 10 to 400, 10 to 500, 50 to 100, 50 to 250, 50 to 500, 100 to 200, 100 to 300, 100 to 400, or 100 to 500 nucleotides apart from one another.

In certain embodiments, a probe is about 5 to 1,000 nucleotides, about 5 to 750 nucleotides, about 5 to 500 nucleotides, about 5 to 250 nucleotides, about 5 to 200 nucleotides, about 5 to 150 nucleotides, about 5 to 100 nucleotides, about 5 to 10 nucleotides, about 5 to 75 nucleotides, about 5 to 500 nucleotides, about 10 to 100 nucleotides, about 10 to 75 nucleotides, about 10 to 50 nucleotides, about 10 to 30 nucleotides, about 5 to 20 nucleotides, about 20 to 100 nucleotides, about 20 to 75 nucleotides, or about 30 to 100 nucleotides in length, or any length in between. In other embodiments, a probe is about 5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length.

In certain embodiments, a probe length is at most 10 nucleotides, 15 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, or 100 nucleotides in length. In other embodiments, a probe is less than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length, but at least 5 nucleotides in length.

Non-limiting examples of probes that can be used in accordance with the methods described herein can be found in U.S. Pat. Nos. 4,851,330, 5,288,611, 5,527,675, 5,539,082, 5,567,587, 5,601,984, 5,612,183, 5,623,049, 5,714,331, 5,719,262, 5,736,336, 5,766,855, 5,773,571, 5,786,461, 5,837,459, 5,891,625, 5,972,610, 5,986,053, 6,083,482, 6,107,470, 6,169,169, 6,174,670, 6,228,982, 6,268,490, 6,280,946, 6,357,163, 6,395,474, 6,441,130, 6,469,151, 6,528,267, 6,639,059, 6,607,889, 6,664,045, 6,670,461, 6,753,421, 7,060,432, 7,214,783, 7,223,833, 7,388,092, and 7,414,118 all of which are incorporated by reference herein.

In specific embodiments, the probes used in the methods described herein hybridize to a nucleic acid sequence comprising ribosomal RNA, e.g., the probes hybridize to a nucleic acid sequence present in 16S ribosomal RNA, a nucleic acid sequence present in 23S ribosomal RNA, a nucleic acid sequence present in 18S ribosomal RNA, or to a nucleic acid sequence present in 28S ribosomal RNA.

In certain embodiments, the probe is specific for bacteria including, but not limited to bacteria of the genus: *Prevotella, Porphyromonas, Borrelia, Mycobacterium, Corynebacterium, Propionibacterium, Mycoplasma, Streptococcus, Listeria, Enterococcus, Staphylococcus, Campylobacter, Bordetella, Burkholderia, Legionella, Acinetobacter, Pseudomonas, Aeromonas, Enterobacter, Klebsiella, Moxarella, Morganella, Proteus, Pantoea, Bartonella, Stenotrophomorias, Actinobacillus, Haemophihis, Escherichia, Klebsiella, Seffatia, Francisella, Raistonia, Shigella, Salmonella,* or *Yersinia.*

In certain embodiments, the probe is specific for virus including, but not limited to, Adenovirus, arbovirus, paramyxovirus, baculovirus, coronavirus, papillomavirus, parvovirus, chickenpox virus, reovirus, Ebola virus, Ebola-like virus, echo virus, encephalitis virus, filovirus, hantavirus, hepatitis virus, German measles virus, cytomegalovirus, hemorrhagic fever virus, herpes simplex virus, human immunodeficiency virus (HIV), human T cell leukemia virus, human T cell lymphoma virus, human T cell lymphotropic virus, influenza virus, Lassa fever virus, Marburg virus, measles virus, mumps virus, myxovirus, nairovirus, nanirnavirus, nariva virus, ndumo virus, Nnecrovirus, neethling virus, neopvirus, neurotropic virus, Newcastle disease virus, oncornavirus, orbivirus, orthomyxovirus, parainfluenza virus, paramyxovirus, parvovirus, picornavirus, rabies virus, respiratory syncytial virus, rhinovirus, rubella virus, rubeola virus, SARS virus, Sendai virus, simian immunodeficiency virus, simian parainfluenza virus, smallpox virus, varicella zoster virus, and variola virus.

In other embodiments, the probe is specific for yeast including, but not limited to yeast of the genus: *Aciculoconidium, Botryoascus, Brettanomyces, Bullera, Bulleromyces, Candida, Citeromyces, Clavispora, Cryptococcus, Cystofilobasidium, Debaromyces, Debaryomyces, Dekkera, Dipodascus, Endomyces, Endomycopsis, Erythrobasidium, Fellomyces, Filobasidium, Guilliermondella, Hanseniaspora, Hansenula, Hasegawaea, Hyphopichia, Issatchenkia, Kloeckera, Kluyveromyces, Komagataella, Leucosporidium, Lipomyces, Lodderomyces, Malassezia—Mastigomyces, Metschnikowia, Mrakia, Nadsonia, Octosporomyces, Oosporidium, Pachysolen, Petasospora, Phaffia, Pichia, Pseudozyma, Rhodosporidium, Rhodotorula, Saccharomyces, Saccharomyeodes, Saccharomycopsis, Schizoblastosporion, Schizosaccharomyces, Schwanniomyces, Selenotila, Sirobasidium, Sporidiobolus, Sporobolomyces, Stephanoascus, Sterigmatomyces, Syringospora, Torulaspora, Torulopsis, Tremelloid, Trichosporon, Trigonopsis, Udeniomyces, Waltomyces, Wickerhamia, Williopsis, Wingea, Yarrowia, Zygofabospora, Zygolipomyces,* or *Zygosaccharomyces.*

In other embodiments, the probe is specific for fungus including, but not limited to: *Blastomyces, Paracoccidiodes, Sporothrix, Cryptococcus, Candida, Aspergillus, Histoplasma, Cryptococcus, Bipolaris, Cladophialophora, Cladosporium, Drechslera, Exophiala, Fonsecaea, Phialophora, Xylohypha, Ochroconis, Rhinocladiella, Scolecobasidium,* and *Wangiella.*

In other embodiments, the probe is specific for parasites including, but not limited to *Babesia, Cryptosporidium, Entamocba histolytica, Leishmania, Giardia lamblia, Plasmodium, Toxoplasma, Trichomonas, Trypanosoma, Ascaris, Cestoda, Ancylostoma, Brugia, Fasciola, Trichinella Schistosoma, Taenia, Cimicidae, Pediculus* and *Sarcoptes.*

Probe Sets. The exemplary methods described herein use pluralities of detectably-labeled, microorganism-specific probe sets. In certain embodiments, these pluralities of detectably-labeled, microorganism-specific probe sets may comprise any number of probe sets desired, wherein each probe set is specific to a different microorganism. For example, a plurality of detectably-labeled, microorganism-specific probe sets may comprise one, two, three, four, five, six, seven, eight, nine, ten, or more than ten probe sets, wherein each probe set is specific to a different microorganism. In other embodiments, these pluralities of detectably-labeled, microorganism-specific probe sets may have any number of probe sets desired, wherein each probe set is specific to a different class of microorganism, e.g., the plurality may have a probe set that has universal probes specific to bacteria, a probe set that has universal probes specific to viruses, and/or a probe set that has universal probes specific to yeast. In certain embodiments, the number of detectable labels in the plurality is less than the number of microorganisms that can be detected by the method.

In certain embodiments, the probes in a detectably-labeled, microorganism-specific probe set may comprise two or more detectable labels, wherein the two or more detectable labels that are at a fixed ratio to one another. Multiple approaches can be utilized to generate probes sets comprising two or more detectable labels are at a fixed ratio to one another. In one example of this embodiment a probe set has two probes for the same target, each with its own detectable label. The two detectably-labeled probes are in a fixed ratio with each other and that fixed ratio determines the signal that indicates the presence of the microorganism target for this probe set.

In yet another preferred embodiment, each probe set contains at least one probe and each probe in the set contains only one detectable label.

In one approach for generating a probe set comprising two or more detectable labels that are at a fixed ratio to one another, the probe set comprises at least a first and a second probe, wherein the first and second probes bind to the same nucleic acid sequence of a microorganism (i.e., the first and second probes are identical), and wherein the first probe comprises one or more molecules of a first detectable label and the second probe comprises one or more molecules of a second detectable label. The fixed ratio between the first and second detectable labels in the probe set is generated as a result of the first and second probes in the probe set comprising varying amounts of detectable labels associated with them. That is, the probe set may comprise one part probes that comprise the molecule of the first detectable label and one part probes that comprise two molecules of the second detectable label, resulting in a probe set with a fixed ratio between the first and second detectable label of 1:2. This approach thus encompasses the use of different amounts of the first and second probe as well as varying numbers of delectable labels associated with each probe to generate different fixed ratios.

In another approach for generating a probe set comprising two or more detectable labels that are at a fixed ratio to one another, the probe set comprises at least a first and a second probe, wherein the first and second probes bind to distinct nucleic acid sequences of the same microorganism, wherein the distinct nucleic acid sequences bound by the probes are present in an equivalent amount, and wherein the first probe comprises one or more molecules of a first detectable label and the second probe comprises one or more molecules of a second detectable label. The fixed ratio between the first and second detectable labels in the probe set is generated as a result of the first and second probes in the probe set comprising varying amounts of detectable labels associated with them. That is, the probe set may comprise one part probes that comprise one molecule of the first detectable label and one part probes that comprise two molecules of the second detectable label, resulting in a probe set with a fixed ratio between the first and second detectable label of 1:2. This approach thus encompasses the use of different amounts of the first and second probe as well as varying numbers of detectable labels associated with each probe to generate different fixed ratios.

In another approach for generating a probe set comprising two or more detectable labels that are at a fixed ratio to one another, the probe set comprises at least a first and a second probe, wherein the first and second probes bind to the same nucleic acid sequence of a microorganism (i.e., the first and second probes are identical), and wherein the first probe comprises a first detectable label and the second probe comprises a second detectable label. The fixed ratio between the first and second detectable labels in the probe set is generated as a result of the probe set comprising varying amounts of the first and second probes. That is, the probe set may comprise one part probes that comprise the first detectable label and two parts probes that comprise the second detectable label, resulting in a probe set with a fixed ratio between the first and second detectable label of 1:2. This approach thus encompasses the use of different amounts of the first and second probe to generate different fixed ratios.

In another approach for generating a probe set comprising two or more detectable labels that are at a fixed ratio to one another, the probe set comprises at least a first and a second probe, wherein the first and second probes bind to distinct nucleic acid sequences of the same microorganism, wherein the distinct nucleic acid sequences bound by the probes are present in equivalent amount, and wherein the first probe comprises a first detectable label and the second probe comprises a second detectable label. The fixed ratio between the first and second detectable labels in the probe set is generated as a result of the probe set comprising varying amounts of the first and second probes. That is, the probe set may comprise one part probes that comprise the first detectable label and two parts probes that comprise the second detectable label, resulting in a probe set with a fixed ratio between the first and second detectable label of 1:2. This approach thus encompasses the use of different amounts of the first and second probe to generate different fixed ratios.

In another approach for generating a probe set comprising two or more detectable labels that are at a fixed ratio to one another, the probe set comprises a first probe that binds to a nucleic acid sequence of a microorganism, wherein the first probe comprises one or more molecules of a first detectable label and one or more molecules of a second detectable label. The fixed ratio between the first and second detectable labels in the probe set is generated as a result of the first probe in the probe set comprising varying amounts of the first and second detectable labels associated with it. That is, the probe set may comprise a first probe that comprises one molecule of the first detectable label and two molecules of the second detectable label, resulting in a probe set with a fixed ratio between the first and second detectable label of 1:2.

The fixed ratios between detectable labels used in the probe sets described herein can be any fixed ratio that can be generated utilized in one or more of the methods described herein. In some embodiments, a fixed ratio is between two different detectable labels in a probe set. In accordance with such embodiments, the fixed ratio may be 1:1, 1:2, 1:3, 2:3 1:4, 3:4 1:5, 2:5, 3:5, 1:6, 1:7, 2:7, 3:7, 4:7, 5:7, 6:7, 1:8, 3:8, 5:8, 7:8, 1:9, 2:9, 4:9, 5:9, 7:9, 8:9, 1:10, 2:10, 3:10, 7:10, 9:10 1:15, 1:20, 1:25, 1:30, 1:35, 1:40, 1:45, 1:50, 1:75, 1:100, or any ratio in between or greater than 1:100. In other embodiments, a fixed ratio is between three different detectable labels in a probe set, wherein the fixed ratio comprises any possible combination of the three detectable labels. In other embodiments, a fixed ratio is between four different detectable labels in a probe set, wherein the fixed ratio comprises any possible combination of the four detectable labels. In other embodiments, a fixed ratio is between five different detectable labels in a probe set wherein the fixed ratio comprises any possible combination of the five detectable labels.

Samples. The samples used in accordance with the methods described herein may be isolated from any source including, but not limited to, a subject (e.g., a human or non-human animal), elements of nature (e.g., water or soil), a beverage, food, a pharmaceutical composition, or a cosmetics composition. A sample may be used in one or more methods described herein immediately after it is isolated from a source or the sample may be subject to manipulation prior to or concurrently with one or more of the methods described herein, e.g., the sample may be contacted with a permeabilizing agent and/or cultured for a period of time before used in one or more of the methods described herein or a portion of the sample may be inoculated into media (e.g., growth media or buffer). In certain embodiments, a sample comprises a portion of the source, i.e., the sample and the source are the same and the sample is an amount of the source (e.g., an aliquot) used in one or more of the methods described herein. In other embodiments, a sample is a component of the source, e.g., blood (sample) isolated from a subject (source). In other embodiments, the entire source is used as the sample in one or more of the methods described herein.

In certain embodiments, a sample is suspected of containing one or more microorganisms, i.e., the sample is isolated from a source that is suspected of being infected by and/or contaminated with one or more microorganisms. In other embodiments, the sample is not suspected of containing one or more microorganisms, but is being tested, e.g., as a means of quality control, to comply with one or more regulations, or to ensure that a source is not infected by and/or contaminated with one or more microorganisms.

Samples used in accordance with one or more of the methods described herein that have been isolated from a source may be processed/manipulated before or during their use in one or more of the methods described herein, or may be used directly in one or more of the methods described herein without any processing/manipulation. For example, a sample may be permeabilized, a sample may be stored (e.g., at room temperature, at 37° C., at 4° C., at −20° C., or at −70° C.), and/or a sample may be cultured (e.g., in medium, in water, or in buffer) before or during their use in one or more of the methods described herein. In certain embodiments, a sample isolated from, obtained from, derived from, or taken from a source is divided into portions, which can be processed/manipulated in the same manner or in a different manner. In some embodiments, a sample is divided into portions and at least one of the sample portions is used in accordance with one or more of the methods described herein, and the remaining sample portions are stored (e.g., at room temperature, at 37° C., at 4° C., at −20° C., or at −70° C.). In other embodiments, a sample is divided into portions, and at least one of the sample portions is used in accordance with one or more of the methods described herein, and the remaining sample portions are cultured (e.g., in medium, in water, or in buffer). In other embodiments, samples may be taken from a source over time as a means to monitor the source for, e.g., the presence of one or more microorganisms.

In certain embodiments, a sample is used in accordance with the methods described herein immediately after it is isolated from a source. In other embodiments, a sample is used in accordance with the methods described herein at most 30 minutes, 1 hour, 2 hours, 4 hours, 6 hours, 8 hours, 12 hours, or 24 hours after it is isolated from a source. In some embodiments, a portion of the sample is used in accordance with the methods described herein immediately after it is isolated from a source, and the remainder of the sample is retained for future use. In accordance with such embodiments, the remaining portion of the sample may be retained at room temperature, or stored, e.g., at 4° C., −20° C., or −70° C.

In some embodiments, after isolating a sample from a source, the sample or a portion of the sample can be used to inoculate media and the inoculated media can be cultured for a certain period of time to allow any microorganisms present in the sample to proliferate. The media chosen as well as the growth conditions (e.g., time and temperature) may depend upon the microorganism being assessed; or the media chosen may be a universal media that is suitable for growth of multiple microorganism types. In certain embodiments, the media is chosen and the growth conditions are selected based on the fact that they will accommodate growth of many different types of microorganisms, e.g., a nutrient-rich, general-purpose medium could be used at a temperature of 37° C. In some embodiments, the culture is for 30 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or greater than 24 hours. In other embodiments, the culture is for less than 30 minutes, less than 1 hour, 1 to 2 hours, 1 to 3 hours, 1 to 5 hours, 1 to 10 hours, 1 to 12 hours, 1 to 24 hours, 2 to 4 hours, 3 to 6 hours, 4 to 8 hours, 6 to 12 hours, 8 to 16 hours, 10 to 20 hours, 12 to 24 hours or 24 to 48 hours.

In certain embodiments, the sample or a portion of a sample is added to a buffer and the sample/buffer mixture is used in accordance with the methods described herein or stored, e.g., at room temperature or at 4° C., at −20° C., or at −70° C. In other embodiments, a portion of a sample is added to sterile water and the sample/water mixture is used in accordance with the methods described herein or stored, e.g., at room temperature or at 4° C., −20° C., or −70° C. In another embodiment, a portion of a sample is added to broth or saline buffer (e.g., AST broth or ID broth sold as part of a kit for the BD Phoenix™ Automated Microbiology System (BD, USA)) and the sample/broth or sample/saline buffer mixture is used in accordance with the methods described herein or stored, e.g., at room temperature or at 4° C., −20° C., or −70° C.

The amount of sample that is isolated from a source will depend on the source. Generally, the amount of sample isolated from a source is an amount that allows for the detection of nucleic acid of a microorganism in accordance with one or more of the methods described herein. In certain embodiments, when the amount of sample isolated from a source is not an amount that allows for the detection of nucleic acid of a microorganism in accordance with one or more of the methods described herein, the sample can be cultured in media suitable for growth of a microorganism until an amount that allows for the detection of nucleic acid of a microorganism is reached. In other embodiments, when the amount of sample isolated from a source is not an amount that allows for the detection of nucleic acid of a microorganism in accordance with one or more of the methods described herein, more sample is isolated from the source. In certain embodiments, the amount of sample is less than 0.001 ml, less than 0.01 ml, less than 0.1 ml, less than 1 ml, less than 5 ml, less than 10 ml, less than 50 ml, less than 100 ml, less than 500 ml, less than 1000 ml, less than 10,000 ml, or less than 100,000 ml. In other embodiments, the sample is more than 0.001 ml, more than 0.01 ml, more than 0.1 ml, more than 1 ml, more than 5 ml, more than 10 ml, more than 50 ml, more than 100 ml, more than 500 ml, more than 1000 ml, more than 10,000 ml, or more than 100,000 ml. In certain embodiments, the sample is less than 0.001 g, less than 0.01 g, less than 0.1 g, less than 1 g, less than 5 g, less than 10 g, less than 50 g, less than 100 g, less than 500 g, less than 1000 g, less than 10,000 g, or less than 100,000 g. In other embodiments, the sample is more than 0.001 g, more than 0.01 g, more than 0.1 g, more than 1 g, more than 5 g, more than 10 g, more than 50 g, more than 100 g. more than 500 g, more than 1000 g, more than 10,000 g, or more than 100,000 g.

In certain embodiments, a sample or portion thereof may be processed in a manner that condenses all or some of the non-liquid portion of the sample, e.g., by centrifugation. In some embodiments, samples of large size in terms of volume can be processed to condense the microorganisms in the sample, whereafter some or all of the liquid portion of the sample can be discarded and the microorganisms can be used directly in one or more of the methods described herein or can be manipulated/processed prior to one or more of the methods described herein, e.g., the microorganisms can be permeabilized, cultured, washed, or resuspended in another media. In other embodiments, samples with non-liquid components other than microorganisms, e.g., food components, blood components, etc., may be processed to condense the non-liquid components other than microorganisms. The remainder of the sample then can be isolated and the non-liquid components other than microorganisms can be discarded.

In certain embodiments, the microorganisms in a sample are subject to permeabilization prior to or concurrently with one or more of the methods described herein. Permeabilization of the microorganisms may be required to allow the probes used in the method access to nucleic acid sequences of the microorganism. Microorganisms can be permeabilized by contacting them with a permeabilizing agent, e.g., is saponin, polyethyleneimine, EDTA, lysozyme, or lysostaphin. In certain embodiments, a sample comprises permeabilized microorganisms. In some embodiments, the process of isolating the sample and/or performing the method may result in permeabilization of the microorganism, thus avoiding the need to permeabilize the microorganism as part of the method. In certain embodiments, when a sample is isolated from living source, e.g., a human, a microorganism may be contained within a host cell from the source (e.g., the microorganism may be contained within a macrophage in the blood of a human host, wherein the blood is the sample). In accordance with such embodiments, a permeabilizing agent may be selected that is capable of permeabilizing both the host cell and the microorganism. In other embodiments, a first permeabilizing agent may be used to permeabilize the host cell and a second penneabilizing agent may be used to permeabilize the microorganism. In some embodiments, the process of isolating the sample and/or performing the method may free the microorganism from the intracellular environment of the host cell, thus avoiding the need to permeabilize the host cell (e.g., the host cell may be lysed during manipulation, thus releasing the microorganism to the extracellular environment). In certain embodiments, the permeabilizing agent selected may vary depending on the type of microorganism present in the sample. For example, when bacteria is believed or determined to be present in the sample, a permeabilizing agent specific for bacteria may be selected. When yeast is believed or determined to be present in the sample, a permeabilizing agent specific for yeast may be selected; etc.

In one embodiment, a sample is isolated from a subject, e.g., a human or a non-human animal. Examples of subjects from which such a sample may be isolated and used in accordance with one or more of the methods presented herein include, but are not limited to, asymptomatic subjects, subjects manifesting or exhibiting 1, 2, 3, 4 or more symptoms of an infection, subjects clinically diagnosed as having an infection, subjects predisposed to infections (e.g., subjects with a genetic predisposition to infections, and/or subjects that lead a lifestyle that predisposes them to infections or increases the likelihood of contracting an infection), subjects suspected of having an infection, subjects undergoing therapy for an infection, subjects with an infection and at least one other condition (e.g., subjects with 2, 3, 4, 5 or more conditions), subjects not undergoing therapy for an infection, and subjects that have not been diagnosed with an infection. In certain embodiments, the subject has been diagnosed as being in or is believed to be in septic shock due to infection by of one or more microorganisms in their body. In one embodiment, the infection is a bacterial infection. In another embodiment, the infection is a viral infection. In another embodiment, the infection is a yeast infection. In yet another embodiment, the infection is a fungal infection. In yet another embodiment, the infection is a parasitic infection.

A sample can be obtained from any tissue or organ in a subject, or any secretion from a subject. Representative samples from a subject include, without limitation, bronchoalveolar lavage, a bronchial wash, a pharyngeal exudate, a tracheal aspirate, a blood sample, a serum sample, a plasma sample, a bone sample, a skin sample, a soft tissue sample, an intestinal tract specimen, a genital tract specimen, breast milk, a lymph sample, cerebrospinal fluid, pleural fluid, a sputum sample, a urine sample, a nasal secretion, tears, a bile sample, an ascites fluid sample, pus, synovial fluid, vitreous fluid, a vaginal secretion, semen, and urethral samples. In some embodiments, two, three or more samples are obtained from a subject. In specific embodiments, two or more samples are obtained from two or more tissues, organs and/or secretions from a subject.

In another embodiment, a sample is isolated from a pharmaceutical source, such as chemicals used in making pharmaceuticals, buffers used in making pharmaceuticals, pharmaceutical compositions used in the treatment of disease, cough and cold medicines, and any other pharmaceutical source that might be produced that is subject to contamination by microorganisms. In another embodiment, a sample is isolated from a cosmetics source, such as a deodorant, perfume, cologne, shampoo, mouthwash, toothpaste, face wash, body wash, and any other cosmetics source that might be produced that is subject to contamination by microorganisms.

In another embodiment, a sample is isolated from a beverage source, such as water, milk, juice, alcohol such as beer, wine, and spirits, spoils drinks, and any other beverage that might be produced that is subject to contamination by microorganisms. In another embodiment, a sample is isolated from a food source, such as salad dressings, condiments, dairy products, meats, poultry, fowl, fruits, vegetables, and any other food source that might be produced that is subject to contamination by microorganisms.

In one embodiment, the sample contains at least the minimum amount of microorganisms required to detect the presence of the microorganism.

In another embodiment, a sample comprises the minimum amount of copies of target nucleic acid of a microorganism required to detect the presence of the microorganism. In one embodiment, a sample comprises at least 500, at least 1,000, at least 1,500, at least 2,000, at least 2,500, at least 3,000, at least 3,500, at least 4,000, at least 4,500, at least 5,000, at least 6,000, at least 7,000, at least 8,000, at least 9,000, or at least 10,000 copies of target nucleic acid of a microorganism. In another embodiment, a sample comprises 500 to 1,000, 1,000 to 2,000, 1,000 to 2,500, 1,000 to 5,000, 1,000 to 10,000, 2,500 to 5,000, 2,500 to 7,500, 2,500 to 10,000, 5,000 to 10,000, or 7,500 to 10,000 copies of target nucleic acid of a microorganism.

In a specific embodiment, a sample comprises at least 10 colony forming units (CFU)/ml, at least $10^2$ CFU/ml, at least 103 CFU/ml, at least 104 CFU/ml, at least 105 CFU/ml, at least 106 CFU/ml, or at least 107 CFU/ml of microorganisms, wherein the microorganisms are bacteria, fungi, or yeast. In another embodiment, a sample comprises about 102 CFU/ml to about 1012 CFU/ml, about 105 CFU/ml to about 1012 CFU/ml, about 106 CFU/ml to about 1012 CFU/ml, or about 107 CFU/ml to about 1012 CFU/ml of microorganisms, wherein the microorganisms are bacteria, fungi, or yeast.

In another specific embodiment, the sample comprises at least 10 particle forming units (PFU)/ml, at least $10^2$ PFU/ml, at least $10^3$ PFU/ml, at least $10^4$ PFU/ml, at least $10^5$ PFU/ml, at least $10^6$ PFU/ml, or at least $10^7$ PFU/ml of microorganisms, wherein the microorganisms are virus. In another embodiment, a sample comprises about $10^2$ PFU/ml to about $10^{12}$ PFU/ml, about $10^6$ PFU/ml to about $10^{12}$ PFU/ml, about $10^6$ PFU/ml to about $10^{12}$ PFU/ml, or about $10^7$ PFU/ml to about $10^{12}$ PFU/ml of microorganisms, wherein the microorganisms are virus.

Detection. Detection of the detectable labels used in accordance with the methods described herein can be accomplished using any approach known in the art, e.g., flow cytometry, solid-phase cytometry, fluoresence microscopy (including imaging), etc.

Flow Cytometery. Flow cytometry is a technique well known in the art that is used for quantitating and examining microscopic particles by suspending them in a stream of fluid and passing them by an electronic detection apparatus. Flow cytometry allows simultaneous multiparametric analysis of the physical and/or chemical characteristics of up to thousands of particles per second.

In flow cytometry, a beam of light (usually laser light) of a single wavelength is directed onto a hydrodynamically-focused stream of fluid. A number of detectors are aimed at the point where the stream passes through the light beam: one in line with the light beam (Forward Scatter or FSC) and several perpendicular to it (Side Scatter (SSC) and one or more fluorescent detectors). Each suspended particle passing through the beam scatters the light in some way, and fluorescent molecules found in the particle or attached to the particle may be excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual particle.

Fluorescence Microscopy. In fluorescence microscopy, the sample being studied is irradiated with light at a specific wavelength. When detectable labels are irradiated with the appropriate specific wavelength, they emit light (fluoresce) and can be detected. The fluorescing areas can be observed in the microscope and shine out against a dark background with high contrast.

Fluorescence-Activated Cell Sorting. Fluorescence-activated cell sorting (FACS) is a specialized type of flow cytometry. Generally, FACS provides a method for sorting a heterogeneous mixture of biological cells into two or more containers, one cell at a time, based upon the specific light scattering and fluorescent characteristics of each cell. Selective optical filters may be employed to allow independent detection, and quantification, of the different individual fluorescent dyes that, as described herein, may be present within a given cell. FACS provides fast, objective and quantitative recording of fluorescent signals from individual cells as well as physical separation of cells of particular interest. Various PACS approaches, e.g., use of the BD PACSArray™, can be used in accordance with the methods described herein as a means of detection.

Solid-Phase Cytometry. Solid-phase cytometry (SPC) is a method by which fluorescently labeled microorganisms present on a substrate, e.g., a slide or filter, can be scanned, detected, and counted (see, e.g., Tarnok et al., 2002, *Cytometry*, 50:133-143). SPC combines a rapid detection system with direct microscopic verification of each fluorescent event and has a detection sensitivity of a single microorganism.

Laser Scanning. Detectable labels used in the methods described herein can be detected using laser scanning, e.g., using a fluorescence laser scanner (see, e.g., in Schena et al., 1996, Genome Res. 6:639-645) or by laser scanning confocal microscopy (e.g., with a confocal laser-scanning microscope).

Characterization of Microorganims. In addition to or in conjunction with the detection of the presence of microorganisms in accordance with the methods described herein, a sample can be characterized using techniques known to those of skill in the art. For example, a sample may be observed for the morphology of the microorganisms and/or different staining reactions may be performed to characterize the microorganisms. The morphological characteristics and staining reactions can aid in the identification of the presence of the microorganisms. In one embodiment, a Gram stain can be performed using techniques known to one of skill in the art to identify whether the microorganism is a Gram-negative or Gram-positive bacteria. In certain embodiments, the Gram stain is performed before a sample is assayed in accordance with the methods described herein. In another embodiment, a method described herein may comprise a probe set comprising probes specific to a particular type of a bacteria, e.g., in the case of bacteria, the method might comprise a probe set that is specific to eukaryotic bacteria. In another embodiment, a method described herein may comprise one or more DNA staining dyes that stain the DNA of a microorganism, e.g., DAPI. The DNA staining dyes may be used to preliminarily identify the type of microorganism present in the sample, e.g., to determine that the microorganism is a bacteria. Alternatively, the DNA staining dyes maybe used to confirm the identity of a microorganism identified by a method described herein.

In certain embodiments, a method described herein may be used in conjunction with methods that allow for the characterization of microorganisms in a sample. For example, in certain embodiments, a method described herein may comprise a probe set comprising probes specific to a gene or gene product (e.g., mRNA) of a microorganism that is known to confer resistance to an antimicrobial compound. In one aspect, the gene or gene product (e.g., mRNA) of the microorganism that confers resistance to an antimicrobial compound is a mecA, aac, aph, aad, armA, rmtA, $bla_{SHV}$, $bla_{TEM}$, ampC, $bla_{ACC}$, mupA, or gyrA gene. In another aspect, the gene confers resistance to a beta-lactam, an aminoglyeosidc, a cephalosproine, mupirocin, or a fluoroquinolone.

Diagnostic Methods. In certain embodiments, provided herein are methods for diagnosing a disease in a subject comprising using one or more of the methods described herein to determine the presence or absence of a microorganism in a sample isolated from a subject and subsequently diagnosing the subject with a disease based on the presence of a given microorganism that is identified in the sample.

Also encompassed herein are methods of monitoring the disease and/or infection in a subject that has been diagnosed with a disease and/or infection based on the presence of a microorganism in a sample isolated from the subject. The disease and/or infection of a subject may be monitored using one or more of the methods provided herein. The disease and/or infection in the subject may be monitored by performing one or more of the methods described herein on a sample isolated from the subject at least once daily, at least twice daily, at least three times daily, or more than three times per day.

In certain embodiments, the presence of a microorganism in a sample isolated from a subject diagnosed with a disease and/or infection is monitored each day following the diagnosis of the disease and/or infection until the presence of the microorganism(s) causing the disease and/or infection is no longer detected. In other embodiments, the presence of a microorganism in a sample isolated from a subject diagnosed with a disease and/or infection is monitored at least once every day, at least once every other day, at least once every three days, at least every five days, at least once every week, at least once every two weeks, at least once every three weeks, at least once every four weeks, or at least once every month following the diagnosis of the disease and/or infection until the presence of the microorganism(s) causing the disease and/or infection is no longer detected. In some embodiments, the presence of a microorganism in a sample isolated from a subject diagnosed with a disease and/or infection is monitored for one day, two days, three days, four days, five days, six days, one week, two weeks, three weeks, four weeks, one month or for greater than one month.

In certain embodiments, the presence of a microorganism in a sample isolated from a subject diagnosed with a disease and/or infection is monitored after the patient has been treated with one or more therapies directed at eradicating the disease and/or infection.

In accordance with the diagnostic methods provided herein, disease caused by any known microorganism can be diagnosed. For example, disease caused by any bacteria, virus, fungi, yeast, or other parasite can be diagnosed using the methods provided herein.

Selection of Therapy. Detection of the presence of a microorganism utilizing the methods presented herein can provide information for the selection of an appropriate therapeutic regimen for a subject diagnosed with a microorganism infection. For example, detecting the presence of a specific microorganism in a sample may indicate what antibiotics should and should not be used to treat an infection caused by the microorganism and suggest alternative therapies, e.g., drugs to which the microorganism is not resistant. In addition to facilitating the appropriate therapeutic regimen for a patient, the detection of the presence of a microorganism in a sample may aid in reducing the transmission of the microorganism from one subject to another.

Quality Control. Detection of the presence of a microorganism utilizing the methods presented herein can provide information regarding the quality of commercial products, e.g., food products, beverage products, pharmaceutical products, cosmetics products, etc. In certain embodiments, the detection of the presence of a microorganism in a commercial product using the methods presented herein indicates that the commercial product is contaminated. In other embodiments, lack of detection of the presence of a microorganism in a commercial product using the methods presented herein indicates that the commercial product is not contaminated. In certain embodiments, the methods provided herein can be used to determine whether the presence of a microorganism in a commercial product is sufficient to meet a certain standard of manufacture, e.g., whether the commercial product contains an acceptable or an unacceptable amount of a microorganism.

In some embodiments, a commercial product is monitored for the presence of a microorganism throughout the manufacturing process of the commercial product. In accordance with such embodiments, the commercial product may be analyzed with one or more of the methods described herein at the beginning of the period of manufacture; at one or more times during the period of manufacture; and/or at the end of the period of manufacture. One or more of the methods described herein could be used as many times as necessary to monitor the commercial product as it is being produced.

Kits. Presented herein are kits comprising, in a container, one or more components required to detect the presence of microorganisms in a sample in accordance with one or more of the methods described herein.

In one embodiment, presented herein are kits comprising a probe set comprising a first probe that is specific to a first microorganism, wherein each first probe in the probe set comprises a first detectable label and a second detectable label.

In another embodiment, presented herein are kits comprising a probe set specific to a microorganism comprising a first and second probe, wherein the first and second probes hybridize to the same nucleic acid sequence, and wherein the first probe comprises a first detectable label and the second probe comprises a second detectable label.

In another embodiment, presented herein are kits comprising a composition that comprises a plurality of microorganism-specific probe sets, wherein (i) said plurality comprises a first and second probe, wherein the first and second probes hybridize to the same nucleic acid sequence, and wherein the first probe comprises a first detectable label and the second probe comprises a second detectable label and (ii) the first and second probes are at a ratio of 2:1 to each other in the composition.

In another embodiment, presented herein are kits comprising a composition that comprises a plurality of microorganism-specific probe sets, wherein (i) said plurality comprises a first and second probe, wherein the first and second probes hybridize to the same nucleic acid sequence, and wherein the first probe comprises a first detectable label and the second probe comprises a second detectable label, (ii) the first and second probes are present in equal concentrations in the composition, and (iii) the first and second detectable labels are at a ratio of 2:1 to each other in the composition.

In another embodiment, presented herein are kits comprising a plurality of microorganism-specific probe sets, wherein said plurality comprises (i) a first probe set specific to a first microorganism, comprising probes labeled with a combination of detectable labels, (ii) a second probe set specific to a second microorganism, comprising probes labeled with a single detectable label, and (iii) a third probe set specific to a third microorganism, comprising probes labeled with a single detectable label; and wherein the total number of detectable labels in the plurality is less than the total number of different microorganisms that can be detected.

In another embodiment, presented herein are kits comprising a plurality of microorganism-specific probe sets, wherein said plurality comprises (i) a first probe set specific to a first microorganism, comprising probes labeled with a combination of detectable labels at a fixed ratio, (ii) a second probe set specific to a second microorganism, comprising probes labeled with a single detectable label, and (iii) a third probe set specific to a third microorganism, comprising probes labeled with a single detectable label; and wherein the total number of detectable labels in the plurality is less than the total number of different microorganisms that can be detected.

In another embodiment, presented herein are kits comprising a plurality of microorganism-specific probe sets, wherein said plurality comprises at least three probe sets, and wherein (i) each probe set is specific to a different microorganism, (ii) the probes in at least one probe set are labeled with a combination of detectable labels, and (iii) the total number of detectable labels in the plurality is less than the total number of different microorganisms that can be detected.

In another embodiment, presented herein are kits comprising a plurality of microorganism-specific probe sets, wherein said plurality comprises at least three probe sets, and wherein (i) each probe set is specific to a different microorganism, (ii) the probes in at least one probe set are labeled with a combination of detectable labels at a fixed ratio, and (iii) the total number of detectable labels in the plurality is less than the total number of different microorganisms that can be detected.

In certain embodiments, the kits described herein further comprise one, two, three, four, or more additional probe sets, wherein each additional probe set is specific to a different microorganism.

In certain embodiments, the kits presented herein further comprise a permeabilizing agent.

The kits presented herein may comprise instructions for using the kits to detect the presence of microorganisms in a sample. In a specific embodiment, the instructions recommend that positive and negative controls are run in parallel with test samples. In some embodiments, the kits presented herein comprise a sample that is known to not hybridize with the probes in one or more of the probe sets provided in the kit (i.e., a negative control). In other embodiments, the kits presented herein comprise a sample that is known to hybridize with the probes in one or more of the probe sets provided in the kit (i.e., a positive control). In yet other embodiments, the kits presented herein comprise a sample that is known to hybridize with the probes in one or more of the probe sets provided in the kit (i.e., a positive control) and a sample that is known to not hybridize with the probes in one or more of the probe sets provided in the kit (i.e., a negative control).

Systems. Presented herein are systems, e.g., automated systems, comprising a kit or a component(s) of the kits presented herein and a computer program product for use in conjunction with a computer system. In such systems, the computer program product can comprise a computer readable storage medium and a computer program mechanism embedded therein. The computer program mechanism may comprise instructions for evaluating the presence of a microorganism, in one or a plurality of samples.

Some systems presented herein comprise a kit or one or more components of the kits presented herein, a computer having a central processing unit and a memory coupled to the central processing unit. Some systems presented herein comprise a kit or one or more components of the kits presented herein, a computer readable medium, a computer having a central processing unit, and a memory coupled to the central processing unit. The memory stores instructions for evaluating the presence of a microorganism. In some embodiments, the memory comprises instructions for transmitting the results of a method presented herein to a remote computer and the remote computer includes instructions for evaluating the presence of a microorganism.

In some embodiments, presented herein is a computer system comprising a computer readable medium comprising the results of an evaluation for the presence of a microorganism. In some embodiments, a computer system presented herein comprises:

a central processing unit;
a main non-volatile storage unit, for example, a hard disk drive, for storing software and data, the storage unit controlled by storage controller;
a system memory, such as high speed random-access memory (RAM), for storing system control programs, data and application programs, comprising programs and data loaded from non-volatile storage unit, and may also include a read-only memory (ROM);
a user interface, comprising one or more input devices (e.g., a keyboard) and display or other output device;
a network interface card for connecting to any wired or wireless communication network (e.g., a wide area network such as the Internet);
an internal bus for interconnecting the aforementioned elements of the system; and
a power source to power the aforementioned elements. Operation of the computer can be controlled primarily by an operating system, which is executed by a central processing unit. The operating system can be stored in the system memory. In addition to the operating system, an implementation system may include one or more of: a file system for controlling access to the various files and data structures presented herein; a training data set for use in the construction of one or more decision rules in accordance with the methods presented herein; a data analysis algorithm module for processing training data and constructing decision rules; one or more decision rules; and a profile evaluation module for determining whether a particular microorganism is present.

The computer may comprise software program modules and data structures. Each of the data structures can comprise any form of a data storage system, including, but not limited to, a flat ASCII or binary file, an Excel spreadsheet, a relational database (e.g., SQL), or an on-line analytical processing (OLAF) database (e.g., MDX and/or variants thereof). In some embodiments, such data structures are each in the form of one or more databases that include a hierarchical structure (e.g., a star schema). In some embodiments, such data structures are each in the form of databases that do not have explicit hierarchy (e.g., dimension tables that are not hierarchically arranged).

In some embodiments, each of the data structures stored or accessible to the computer system are single data structures. In other embodiments, such data structures in fact comprise a plurality of data structures (e.g., databases, files, archives) that may or may not all be hosted by the same computer. For example, in some embodiments, a training data set may comprise a plurality of Excel spreadsheets that are stored either on the computer and/or computers that are addressable by the computer across wide area network. In another example, a training set may comprise a database that is either stored on the computer or is distributed across one or more computers that are addressable by the computer across a wide area network.

It will be appreciated that many of the modules and data structures mentioned above can be located on one or more remote computers. For example, in some embodiments, web service-type implementations are used. In such embodiments, an evaluation module can reside on a client computer that is in communication with the computer via a network. In some embodiments, a profile evaluation module can be an interactive web page.

In some embodiments, a training data set and/or decision rules are on a single computer and in other embodiments, one or more of such data structures and modules are hosted by one or more remote computers. Any arrangement of the data structures and software modules on one or more computers is within the scope the systems presented herein so long as these data structures and software modules are addressable with respect to each other across a network or by other electronic means.

In some embodiments, a digital signal embodied on a carrier wave comprises data with respect to a method presented herein. In some embodiments, a digital signal embodied on a carrier wave comprises a determination as to whether a particular microorganism is present in a sample. In some embodiments, a graphical user interface is provided for determining whether a microorganism is present in a sample. The graphical user interface may comprise a display field for displaying a result encoded in a digital signal embodied on a carrier wave received from a remote computer.

EXAMPLE 1

In one exemplary embodiment, combinatorial FISH is used to detect seven different species of organisms. The microorganisms are identified in Table 2 below. The seven probe sets are designed according to methods known in the art to select (i.e. hybridize) to one microorganism preferentially over the other microorganisms. Each probe set has one or more probes having a target binding sequence that selects for the nucleotide sequence of the microorganism to which the probe set is configured to hybridize. In this example, the probes in the exemplary probe sets are configured to hybridize to the rRNA of the microorganism that the probe set is designed to detect.

FIG. 1 graphically illustrates the details of the present example. Each probe set contains multiple copies of at least one probe specific for the target rRNA sequence for a specific microorganism. Each labeled probe has a single detectable label (e.g. a dye). In some instances, the probes in a given probe set are divided into more than one group. In Instances where this occurs, a first group of identical probes is labeled with a first dye, a second group is labeled with a second dye, etc. One probe set in this example is divided into three separate groups of identical probes. Each group of probes is labeled with a different dye (i.e. the first group is labeled with a first dye, the second group is labeled with a second dye and the third group is labeled with a third dye).

The method described in this example is useful for detecting the presence or absence of different species of a microorganism in addition to distinguishing between different microorganisms. The microorganisms, probe sequences and corresponding dyes are set forth in Table 2. The microorganism targets are not expressly stated, but references that describe the microorganism targets are identified in Table 2 below and those references are incorporated by reference herein.

TABLE 2

Materials for Multiplexed Detection of Seven (7) Organisms with 3 Dyes by Combinatorial FISH

| Probe Set | Target Organism | Probe Name; target region; reference where described | SEQ ID Number | Probe Target Binding Sequence | Label Configuration |
|---|---|---|---|---|---|
| 1 | S. aureus | Sta; 16s rRNA, Kempf et al 2000 | SEQ ID NO. 1 | gaagcaagcttctcgtccg | Single dye (FITC) |
| 2 | Coag. Neg. Staph | Sau; 16s rRNA; Kempf et al 2000 | SEQ ID NO. 2 | cgacggctagctccaaatggt tact | Single Dye (ROX) |
| 3 | E. faecalis | Efs; 23s rRNA; Kempf et al 2000 | SEQ ID NO. 3 | ccccttctgatgggcagg | Single Dye (Cy5) |
| 4 | S. pnuemoniae | Spn; 16s rRNA, Kempf et al 2000 | SEQ ID NO. 4 | gtgatgcaagtgcacctt | 2-Dye Ensemble (First Group-FITC and Second Group-ROX) |
| 5 | E. coli | ECOLI; 16s rRNA; Jansen et al 2000 | SEQ ID NO. 5 | gcaaaggtattaactttactc cc | 2-Dye Ensemble (First Group-FITC and Second Group-Cy5) |
| 6 | K. pnuemoniae | Kpn; 23s rRNA; Kempf et al 2000 | SEQ ID NO. 6 | cctacacaccagcgtgcc | 2-Dye Ensemble (First Group-ROX and Second Group-Cy5) |

TABLE 2-continued

Materials for Multiplexed Detection of Seven (7)
Organisms with 3 Dyes by Combinatorial FISH

| Probe Set | Target Organism | Probe Name; target region; reference where described | SEQ ID Number | Probe Target Binding Sequence | Label Configuration |
|---|---|---|---|---|---|
| 7 | P. aeruginosa | Psae; 23s rRNA; Kempf et al 2000 | SEQ ID NO. 7 | tctcggccttgaaacccc | 3-Dye Ensemble (First Group-FITC, Second Group-ROX, Third Group-Cy5) |

As seen in FIG. 1, seven distinct probe sets are deployed in this example. However, only three different labels, in different combinations for different probe sets are used to provide a distinct signal indicating the presence or absence of one of the microorganisms in the sample. The labels used in this example, and as set forth in Table 2 are: FITC; ROX and Cy5. Fluorescence of any of these dyes, either by themselves, or in combination with one or more other dyes, will indicate the presence of a particular targeted microorganism. Lack of fluorescence of the dye or particular dye combination associated with a particular microorganism indicates that the particular microorganism is absent from the sample.

Probe Set 1, specific for S. aureus, has detectably labeled probes with the target binding sequence SEQ ID NO.1. All of the labeled probes in Probe Set 1 are labeled with FITC. Probe Set 2, specific for Coag. Neg. Staph, has detectably labeled probes with the target binding sequence SEQ ID NO. 2. All of the labeled probes in Probe Set 2 are labeled with ROX. Probe set 3, specific for E. faecalis, has a detectably labeled probe with the target binding sequence SEQ ID No. 3. All of the labeled probes in probe set 3 are labeled with Cy5.

Probe Set 4, specific for S. pneumonia, has detectably labeled probes with a target binding sequence that is SEQ ID NO 4. In probe set 4, half of the labeled probes are labeled with FITC and the other half of the labeled probes are labeled with ROX.

Probe Set 5, specific for E. Coli, has detectably labeled probes having the target binding sequence SEQ ID NO 5. In probe set 5, half of the labeled probes are labeled with FITC and the other half of the labeled probes are labeled with Cy5. Probe Set 6, specific for K. pneumonia, has detectably labeled probes having a target binding sequence that is SEQ ID NO 6. In probe set 6, half of the labeled probes are labeled with Cy5 and half of the labeled probes are labeled with ROX.

Probe set 7, specific for P. aeruginosa, has detectably labeled probes having the target binding sequence that is SEQ ID NO. 7. In probe set 7, one third of the labeled probes are labeled with FITC, one third of the labeled probes are labeled with ROX and one third of the labeled probes are labeled with Cy5.

As is also well known in the art, FITC will fluoresce as a green color (maximum emission at ~520 nm), while ROX fluoresces as a yellow color (maximum florescence at ~605 nm) and Cy5 fluoresces as red (maximum florescence at ~667 nm). Therefore, the fluorescence intensity of each dye can be measured, and quantified, independently from the other dyes by employing optical filters that are selective for light emitted at specific wavelengths. Thus, by varying the ratios of dyes between different probes sets and quantifying the fluorescence intensity at the wavelengths characteristic of each dye, the number of uniquely labeled probe sets can exceed the 7 probe sets set forth in Example 1. For example, while Probe set 7 in Example 1 contains a 1:1:1 ratio of FITC:ROX:Cy5, additional probe sets could contain FITC:ROX:Cy5 ratios of 1:1:2, 1:2:1, or 2:1:1, thereby expanding possible number of uniquely detectable probe sets from 7 to 10. Likewise, ratios of FITC:ROX, FITC:Cy5, and ROX:Cy5 could be varied to expand the number of uniquely detectable two-dye probe sets. To produce a probe set containing a particular dye ratio, individual probes, each labeled with a single dye, can be simply mixed together in the desired ratio. Analysis and detection of the probe sets discussed herein can be accomplished by methods well known to one of ordinary skill in the art. Those methods include but are not limited to flow cytometry and fluorescence microscopy.

As shown in FIG. 1, once the labeled probes hybridize to their respective targets, fluorescence can be detected indicating the presence of a particular microorganism. If no fluorescence is detected, then the absence of the microorganism is indicated. The probe sets can be combined with a given sample in order to detect multiple microorganisms in the sample. One advantage to this approach is that a wide array of distinct signals can be achieved using a few different detectable labels. Probe/dye synthesis is simplified as there is only one dye per probe.

In an alternative to Example 1, multiple probes in the probe set have different target binding sequences for the target microorganism. The labeled probes in these probe sets each have one detectable label (e.g. a dye). Therefore, in this example, the labeled probes in a given probe set do not compete for the same target sequence in the microorganism. As in the previous example, one example of target nucleic sequences in the target microorganism are rRNA sequences, but any nucleic acid sequence within the target microorganism can be the target for the probe sets described herein. One advantage of probe sets containing labeled probes with different target binding sequences for the target microorganism is the generation of a stronger fluorescence signal, since the probes do not compete for the same target sequence.

Those skilled in the art will recognize, or be able to ascertain using no more than routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

What is claimed is:

1. A method for detecting the presence of microorganisms in a sample, comprising:
   (a) contacting the sample with a plurality of detectably-labeled, microorganism-specific probe sets, wherein said plurality comprises a first probe set specific to a nucleic acid sequence of a first microorganism comprising a first and a second probe, and wherein (i) the first and second probes hybridize to the same nucleic acid sequence, (ii) the first probe comprises a first detectable label and the second probe comprises a second detectable label, and (iii) the first and second detectable labels are at a first fixed ratio, and wherein the plurality of detectably-labeled, microorganism-specific probe sets further comprises a second probe set specific to a nucleic acid sequence of a second microorganism comprising a first and second probe, wherein the first and second probes hybridize to the same nucleic acid sequence of the second microorganism, and wherein (i) the first probe comprises the first detectable label and the second probe comprises the second detectable label and (ii) the first and second detectable labels in the second probe set are at a second fixed ratio that is different than the first fixed ratio of the first and second detectable labels in the first probe set; under conditions that allow hybridization of the probes to the nucleic acid sequence of the microorganism; and
   (b) assaying for the presence of a hybridized probe set, wherein the first detectable label in the first and second probe sets is the same and the second detectable label in the first and second probe sets is the same; and wherein the first fixed ratio of the first and second detectable probes indicates the presence in the sample of the first microorganism and the second fixed ratio of the first and second detectable labels provides a signal that indicates the presence of the second microorganism in the sample.

2. The method of claim 1, wherein the plurality of detectably-labeled, microorganism-specific probe sets comprises a third probe set specific to a third microorganism comprising a first and second probe, wherein the first and second probes hybridize to the same nucleic acid sequence of the third microorganism, and wherein (i) the first probe comprises the first detectable label and the second probe comprises the second detectable label and (ii) the first and second detectable labels in the third probe set are at a different fixed ratio than the first and second detectable labels in the first and second probe sets.

3. The method of claim 2, wherein the plurality of detectably-labeled, microorganism-specific probe sets comprises a fourth probe set specific to a fourth microorganism comprising a first and second probe, wherein the first and second probes hybridize to the same nucleic acid sequence of the fourth microorganism, and wherein (i) the first probe comprises the first detectable label and the second probe comprises the second detectable label and (ii) the first and second detectable labels in the fourth probe set are at a different fixed ratio than the first and second detectable labels in the first, second, and third probe sets.

4. The method of claim 1, wherein the difference in fixed ratios is due to the amounts of the first and second probe in each probe set.

5. The method of claim 1, wherein the difference in fixed ratios is due to the amount of detectable label associated with the first and/or second probe in each probe set.

6. The method of claim 1 wherein the ratio is 1:1, 2:1, 3:1, 4:1, 5:1,6:1: 7:1,8:1, 9:1, 10:1.

7. A method for detecting the presence of microorganisms in a sample, comprising:
   (a) contacting the sample with a plurality of detectably-labeled, microorganism-specific probe sets, wherein said plurality comprises (i) a first probe set comprising first and second probes each specific to a first microorganism, the first and second probes having first and second detectable labels, the first and second detectably labeled probes being different from each other and at a first fixed ratio, (ii) a second probe set specific to a second microorganism, comprising third and fourth probes each labeled with a different one of first and second labels at a second fixed ratio and (iii) a third probe set specific to a third microorganism, comprising probes labeled with a detectable label that are the same as or different from the first and second detectable labels and, if the same, are at a different fixed ratio than the first and second detectably labeled probes in the probe sets for the first and second microorganism; and wherein the total number of detectable labels in the plurality is less than the total number of different microorganisms that can be detected by the first, second and third probe sets; under conditions that allow hybridization of the probes to a nucleic acid sequence of a microorganism; and
   (b) assaying for the presence of a hybridized probe set, wherein the first fixed ratio of the first and second detectably labelled probes provides a signal that indicates the presence of the first microorganism in the sample and the second fixed ratio of the third and fourth detectably labelled probes indicates the presence of the second microorganism in the sample.

8. A method for detecting the presence of microorganisms in a sample, comprising:
- (a) contacting the sample with a plurality of detectably-labeled, microorganism-specific probe sets, wherein said plurality comprises at least three probe sets, and wherein (i) each probe set is specific to a different microorganism, (ii) at least two probe sets comprise at least two detectably labelled probes, the first probes in the at least two probe sets are each labeled with the same first detectable label and the second probes in at least two probes sets are labeled with a second detectable label wherein the ratio of first and second detectably labelled probes in the first probe set is different from the ratio of first and second detectably labelled probes in the second probe set, and (iii) the total number of detectable labels in the at least three probes sets is less than the total number of different microorganisms that can be detected; under conditions that allow hybridization of the probes to a nucleic acid sequence of a microorganism; and
- (b) assaying for the presence of a hybridized probe set, wherein the fixed ratio of the first and second detectable probes in the first probe set indicates the presence in the sample of a first microorganism for which the first probe set is specific and the fixed ratio of the first and second detectable probes in the second probe set indicates the presence in the sample of a second microorganism for which the second probe set is specific.

9. The method of claim 8, wherein the plurality of detectably-labeled, microorganism-specific probe sets comprises a fourth probe set specific to a fourth microorganism.

10. The method of claim 9, wherein the probes in the fourth probe set are labeled with a combination of detectable labels at a fixed ratio.

11. The method of claim 9, wherein the plurality of detectably-labeled, microorganism-specific probe sets comprises a fifth probe set specific to a fifth microorganism.

12. The method of claim 11, wherein the probes in the fifth probe set are labeled with a combination of detectable labels at a fixed ratio.

13. The method of claim 11, wherein the plurality of detectably-labeled, microorganism-specific probe sets comprises a sixth probe set specific to a sixth microorganism.

14. The method of claim 13, wherein the probes in the sixth probe set are labeled with a combination of detectable labels at a fixed ratio.

15. The method of claim 13, wherein the plurality of detectably-labeled, microorganism-specific probe sets comprises a seventh probe set specific to a seventh microorganism.

16. The method of claim 15, wherein the probes in the seventh probe set are labeled with a combination of detectable labels at a fixed ratio.

17. The method of claim 8, wherein the probes in the first, second, and third probe sets are each complementary to a single nucleic acid sequence of the respective first microorganism, the second microorganism, and the third microorganism.

18. The method of claim 8, wherein the first, second, and third probe sets each comprise probes that are complementary to more than one nucleic acid sequence of the first microorganism, the second microorganism, and the third microorganism, respectively.

* * * * *

```
                          SEQUENCE LISTING

<160> NUMBER OF SEQ ID NOS: 7

<210> SEQ ID NO 1
  <211> LENGTH: 19
  <212> TYPE: DNA
  <213> ORGANISM: Artificial Sequence
  <220> FEATURE:
  <223> OTHER INFORMATION: Synthetic Probe

<400> SEQUENCE: 1
gaagcaagct tctcgtccg                                              19

<210> SEQ ID NO 2
  <211> LENGTH: 25
  <212> TYPE: DNA
  <213> ORGANISM: Artificial Sequence
  <220> FEATURE:
  <223> OTHER INFORMATION: Synthetic Probe

<400> SEQUENCE: 2
cgacggctag ctccaaatgg ttact                                       25

<210> SEQ ID NO 3
  <211> LENGTH: 18
  <212> TYPE: DNA
  <213> ORGANISM: Artificial Sequence
  <220> FEATURE:
  <223> OTHER INFORMATION: Synthetic Probe

<400> SEQUENCE: 3 cccctttctga tgggcagg                                              18

<210> SEQ ID NO 4
  <211> LENGTH: 18
  <212> TYPE: DNA
  <213> ORGANISM: Artificial Sequence
  <220> FEATURE:
  <223> OTHER INFORMATION: Synthetic Probe

<400> SEQUENCE: 4
gtgatgcaag tgcacctt                                               18

<210> SEQ ID NO 5
  <211> LENGTH: 23
  <212> TYPE: DNA
  <213> ORGANISM: Artificial Sequence
  <220> FEATURE:
  <223> OTHER INFORMATION: Synthetic Probe

<400> SEQUENCE: 5
gcaaaggtat taactttact ccc                                         23

<210> SEQ ID NO 6
  <211> LENGTH: 18
  <212> TYPE: DNA
  <213> ORGANISM: Artificial Sequence
  <220> FEATURE:
  <223> OTHER INFORMATION: Synthetic Probe
```

```
<400> SEQUENCE: 6
cctacacacc agcgtgcc                                              18

<210> SEQ ID NO 7
<211> LENGTH: 18
<212> TYPE: DNA
<213> ORGANISM: Artificial Sequence
<220> FEATURE:
<223> OTHER INFORMATION: Synthetic Probe

<400> SEQUENCE: 7
tctcggcctt gaaacccc                                              18
```